United States Patent
Halldorsson et al.

(10) Patent No.: US 9,044,348 B2
(45) Date of Patent: Jun. 2, 2015

(54) PROSTHETIC DEVICE, SYSTEM AND METHOD FOR INCREASING VACUUM ATTACHMENT

(71) Applicant: OSSUR HF, Reykjavik (IS)

(72) Inventors: Olafur Freyr Halldorsson, Reykjavik (IS); David Sandahl, Seltjarnarnes (IS); Bjarni Gunnarsson, Reykjavik (IS); Egill Sveinbjorn Egilsson, Reykjavik (IS)

(73) Assignee: OSSUR HF, Reykjavik (IS)

( * ) Notice: Subject to any disclaimer, the term of this patent is extended or adjusted under 35 U.S.C. 154(b) by 83 days.

(21) Appl. No.: 13/873,394

(22) Filed: Apr. 30, 2013

(65) Prior Publication Data

US 2013/0289742 A1    Oct. 31, 2013

Related U.S. Application Data

(60) Provisional application No. 61/683,245, filed on Aug. 15, 2012, provisional application No. 61/762,097, filed on Feb. 7, 2013, provisional application No. 61/640,056, filed on Apr. 30, 2012.

(51) Int. Cl.
| | |
|---|---|
| *A61F 2/66* | (2006.01) |
| *A61F 2/80* | (2006.01) |
| *A61F 2/68* | (2006.01) |

(Continued)

(52) U.S. Cl.
CPC ... *A61F 2/80* (2013.01); *A61F 2/68* (2013.01); *A61F 2/66* (2013.01); *A61F 2002/501* (2013.01); *A61F 2002/5067* (2013.01); *A61F 2002/5079* (2013.01); *A61F 2002/607* (2013.01); *A61F 2002/6614* (2013.01); *A61F 2002/6664* (2013.01); *A61F 2002/742* (2013.01); *A61F 2002/802* (2013.01)

(58) Field of Classification Search
USPC .............................................. 623/36, 53–56
See application file for complete search history.

(56) References Cited

U.S. PATENT DOCUMENTS

| 708,685 A | 9/1902 | White |
| 980,457 A | 1/1911 | Toles |

(Continued)

FOREIGN PATENT DOCUMENTS

| AU | 670631 | 7/1996 |
| BE | 675386 | 5/1966 |

(Continued)

OTHER PUBLICATIONS

U.S. Appl. No. 09/325,297, filed Jun. 3, 1999, Caspers.
U.S. Appl. No. 09/670,853, filed Sep. 27, 2000, Caspers.
U.S. Appl. No. 09/829,306, filed Apr. 9, 2001, Caspers.
U.S. Appl. No. 10/615,203, filed Jul. 7, 2003, Caspers.
U.S. Appl. No. 10/740,938, filed Dec. 17, 2003, Caspers.

(Continued)

*Primary Examiner* — Bruce E Snow
(74) *Attorney, Agent, or Firm* — Workman Nydegger

(57) ABSTRACT

A prosthetic device, system and method is arranged to generate negative pressure inside a prosthetic socket. A pump mechanism is connected to a prosthetic foot and has a fluid chamber in fluid communication with the prosthetic socket during gait for drawing air from the prosthetic socket in step phase, and expelling air into the atmosphere in swing phase. The vacuum assisted suspension results in secure and intimate suspension as the negative pressure formed inside the prosthetic socket holds a residuum firmly to walls of the prosthetic socket. The vacuum is preferably formed at the distal area of the prosthetic socket, and sealed by a suspension liner having a seal component.

8 Claims, 11 Drawing Sheets

(51) Int. Cl.
*A61F 2/50* (2006.01)
*A61F 2/60* (2006.01)
*A61F 2/74* (2006.01)

(56) References Cited

U.S. PATENT DOCUMENTS

| | | | |
|---|---|---|---|
| 1,288,803 A | 12/1918 | Beck |
| 1,586,015 A | 5/1926 | Underwood |
| 2,424,278 A | 7/1947 | Kunkel |
| 2,464,443 A | 3/1949 | Ganoe |
| 2,530,285 A | 11/1950 | Catranis |
| 2,533,404 A | 12/1950 | Sharp |
| 2,606,325 A | 8/1952 | Nielson |
| 2,664,572 A | 1/1954 | Blevens |
| 2,671,225 A | 3/1954 | Schoene |
| 2,696,010 A | 12/1954 | Robinson |
| 2,696,011 A | 12/1954 | Galdik |
| 2,790,180 A | 4/1957 | Hauser |
| 2,808,593 A | 10/1957 | Andersen |
| 3,253,600 A | 5/1966 | Scholl |
| 3,322,873 A | 5/1967 | Hitchcock |
| 3,377,416 A | 4/1968 | Kandel |
| 3,396,407 A | 8/1968 | Kandel |
| 3,557,387 A | 1/1971 | Ohlenbusch |
| 3,631,542 A | 1/1972 | Potter |
| 3,712,298 A | 1/1973 | Snowdon |
| 3,732,578 A | 5/1973 | Pollack |
| 3,751,733 A | 8/1973 | Fletcher |
| 3,806,958 A | 4/1974 | Gusev |
| 3,858,379 A | 1/1975 | Graves |
| 3,889,301 A | 6/1975 | Bonner |
| 3,895,405 A | 7/1975 | Edwards |
| 3,922,727 A | 12/1975 | Bianco |
| 3,975,350 A | 8/1976 | Hudgin |
| 3,991,424 A | 11/1976 | Prahl |
| 4,010,052 A | 3/1977 | Edwards |
| 4,106,745 A | 8/1978 | Carrow |
| 4,133,776 A | 1/1979 | Pruett |
| 4,282,325 A | 8/1981 | Rubenstein |
| 4,283,800 A | 8/1981 | Wilson |
| 4,314,398 A | 2/1982 | Pettersson |
| 4,381,768 A | 5/1983 | Erichsen |
| 4,404,296 A | 9/1983 | Schapel |
| 4,456,642 A | 6/1984 | Burgdorfer |
| 4,466,936 A | 8/1984 | Schapel |
| 4,479,272 A | 10/1984 | Beldzisky |
| 4,623,354 A | 11/1986 | Childress |
| 4,634,446 A | 1/1987 | Kristinsson |
| 4,635,626 A | 1/1987 | Lerman |
| 4,655,779 A | 4/1987 | Janowiak |
| 4,704,129 A | 11/1987 | Massey |
| 4,822,371 A | 4/1989 | Jolly |
| 4,828,325 A | 5/1989 | Brooks |
| 4,888,829 A | 12/1989 | Kleinerman |
| 4,908,037 A | 3/1990 | Ross |
| 4,923,475 A | 5/1990 | Gosthnian |
| 5,007,937 A | 4/1991 | Fishman |
| 5,108,455 A | 4/1992 | Telikicherla |
| 5,108,456 A | 4/1992 | Coonan |
| 5,133,776 A | 7/1992 | Crowder |
| 5,139,523 A | 8/1992 | Paton |
| 5,163,965 A | 11/1992 | Rasmusson |
| 5,201,774 A | 4/1993 | Greene |
| 5,211,667 A | 5/1993 | Danforth |
| 5,221,222 A | 6/1993 | Townes |
| 5,258,037 A | 11/1993 | Caspers |
| 5,314,497 A | 5/1994 | Fay |
| 5,353,525 A | 10/1994 | Grim |
| 5,362,834 A | 11/1994 | Schapel |
| 5,376,129 A | 12/1994 | Faulkner |
| 5,376,131 A | 12/1994 | Lenze |
| 5,376,132 A | 12/1994 | Caspers |
| 5,397,628 A | 3/1995 | Crawley |
| 5,405,407 A | 4/1995 | Kodama |
| 5,480,455 A | 1/1996 | Norvell |
| 5,490,537 A | 2/1996 | Hill |
| 5,507,834 A | 4/1996 | Laghi |
| 5,534,034 A | 7/1996 | Caspers |
| 5,549,709 A | 8/1996 | Caspers |
| 5,555,216 A | 9/1996 | Drouot |
| 5,571,208 A | 11/1996 | Caspers |
| 5,593,454 A | 1/1997 | Helmy |
| D379,845 S | 6/1997 | Lee |
| 5,658,353 A | 8/1997 | Layton |
| 5,658,354 A | 8/1997 | Norvell |
| 5,702,488 A | 12/1997 | Wood et al. |
| 5,702,489 A | 12/1997 | Slemker |
| 5,709,017 A | 1/1998 | Hill |
| 5,728,166 A | 3/1998 | Slemker |
| 5,728,167 A | 3/1998 | Lohmann |
| 5,728,168 A | 3/1998 | Laghi |
| 5,728,169 A | 3/1998 | Norvell |
| 5,728,170 A | 3/1998 | Becker |
| 5,732,578 A | 3/1998 | Kang |
| 5,735,906 A | 4/1998 | Caspers |
| 5,807,303 A | 9/1998 | Bays |
| 5,830,237 A | 11/1998 | Kania |
| 5,846,063 A | 12/1998 | Lakic |
| 5,888,216 A | 3/1999 | Haberman |
| 5,888,230 A | 3/1999 | Helmy |
| 5,888,231 A | 3/1999 | Sandvig |
| 5,904,721 A | 5/1999 | Henry |
| 5,904,722 A | 5/1999 | Caspers |
| 5,931,872 A | 8/1999 | Lohmann |
| 5,980,577 A | 11/1999 | Radis |
| 5,984,972 A | 11/1999 | Huston et al. |
| 6,007,582 A | 12/1999 | May |
| 6,063,125 A | 5/2000 | Arbogast |
| 6,066,107 A | 5/2000 | Habermeyer |
| D429,335 S | 8/2000 | Caspers |
| 6,117,117 A | 9/2000 | Mauch |
| 6,149,691 A | 11/2000 | Fay et al. |
| 6,231,616 B1 | 5/2001 | Helmy |
| 6,231,617 B1 | 5/2001 | Fay |
| 6,273,918 B1 | 8/2001 | Yuhasz |
| 6,287,345 B1 | 9/2001 | Slemker |
| 6,296,669 B1 | 10/2001 | Thorn et al. |
| 6,334,876 B1 | 1/2002 | Perkins |
| 6,361,568 B1 | 3/2002 | Hoerner |
| 6,362,387 B1 | 3/2002 | Carlson et al. |
| 6,402,788 B1 | 6/2002 | Wood |
| 6,406,499 B1 | 6/2002 | Kania |
| 6,508,842 B1 | 1/2003 | Caspers |
| 6,544,292 B1 | 4/2003 | Laghi |
| 6,554,868 B1 | 4/2003 | Caspers |
| 6,602,295 B1 | 8/2003 | Doddroe et al. |
| 6,613,096 B1 | 9/2003 | Shirvis |
| 6,626,952 B2 | 9/2003 | Janusson et al. |
| 6,645,253 B2 | 11/2003 | Caspers |
| 6,673,117 B1 | 1/2004 | Soss |
| 6,702,858 B2 | 3/2004 | Christensen |
| 6,706,364 B2 | 3/2004 | Janusson et al. |
| 6,726,726 B2 | 4/2004 | Caspers |
| 6,761,742 B2 | 7/2004 | Caspers |
| 6,767,370 B1 | 7/2004 | Mosler |
| 6,797,008 B1 | 9/2004 | Arbogast et al. |
| D499,794 S | 12/2004 | Comer |
| 6,855,170 B2 | 2/2005 | Gramnas |
| 6,863,695 B2 | 3/2005 | Doddroe |
| 6,926,742 B2 | 8/2005 | Caspers |
| 6,964,688 B1 | 11/2005 | Kania |
| 6,974,484 B2 | 12/2005 | Caspers |
| 7,025,792 B2 | 4/2006 | Collier |
| D526,046 S | 8/2006 | Lin |
| 7,255,131 B2 | 8/2007 | Paper et al. |
| 7,427,297 B2 | 9/2008 | Patterson et al. |
| 7,448,407 B2 | 11/2008 | Alley et al. |
| 7,468,079 B2 | 12/2008 | Collier |
| 7,686,848 B2 | 3/2010 | Christensen |
| 7,744,653 B2 | 6/2010 | Rush |
| D634,813 S | 3/2011 | Hernandez, IV |
| 7,922,775 B2 | 4/2011 | Caspers |
| 7,947,085 B2 | 5/2011 | Haines |
| D639,825 S | 6/2011 | Murakami et al. |

(56) References Cited

U.S. PATENT DOCUMENTS

| | | | |
|---|---|---|---|
| 7,993,413 | B2 | 8/2011 | Perkins et al. |
| 8,007,543 | B2 | 8/2011 | Martin |
| 8,097,766 | B2 | 1/2012 | Carlson et al. |
| 8,114,167 | B2 | 2/2012 | Caspers |
| D655,393 | S | 3/2012 | Whitaker |
| D656,223 | S | 3/2012 | Cronje et al. |
| 8,298,294 | B2 | 10/2012 | Kaltenborn |
| 8,317,876 | B2 | 11/2012 | Mosler |
| 8,343,233 | B2 | 1/2013 | Perkins et al. |
| D675,714 | S | 2/2013 | Nguyen |
| D681,782 | S | 5/2013 | Bohm et al. |
| 8,523,951 | B2 | 9/2013 | Kania |
| D691,240 | S | 10/2013 | Iranyi et al. |
| D691,701 | S | 10/2013 | Iranyi et al. |
| D691,702 | S | 10/2013 | Iranyi et al. |
| D691,703 | S | 10/2013 | Iranyi et al. |
| D702,320 | S | 4/2014 | Pifer |
| 2001/0005798 | A1 | 6/2001 | Caspers |
| 2001/0016781 | A1 | 8/2001 | Caspers |
| 2002/0087215 | A1 | 7/2002 | Caspers |
| 2002/0091449 | A1 | 7/2002 | Caspers et al. |
| 2002/0103545 | A1 | 8/2002 | Arbogast et al. |
| 2002/0128580 | A1 | 9/2002 | Carlson et al. |
| 2003/0191539 | A1 | 10/2003 | Caspers |
| 2004/0024322 | A1 | 2/2004 | Caspers |
| 2004/0064195 | A1 | 4/2004 | Herr |
| 2004/0163278 | A1 | 8/2004 | Caspers |
| 2004/0181290 | A1 | 9/2004 | Caspers |
| 2004/0236434 | A1 | 11/2004 | Carstens |
| 2004/0260403 | A1 | 12/2004 | Patterson et al. |
| 2005/0131549 | A1 | 6/2005 | Caspers |
| 2005/0143838 | A1 | 6/2005 | Collier |
| 2005/0240282 | A1 | 10/2005 | Rush et al. |
| 2006/0212130 | A1 | 9/2006 | Collier |
| 2006/0212131 | A1 | 9/2006 | Curtis |
| 2007/0005149 | A1 | 1/2007 | Egilsson et al. |
| 2007/0043316 | A1 | 2/2007 | Carlson et al. |
| 2007/0055383 | A1 | 3/2007 | King |
| 2007/0112440 | A1 | 5/2007 | Perkins et al. |
| 2007/0196222 | A1 | 8/2007 | Mosler |
| 2008/0269911 | A1 | 10/2008 | Street et al. |
| 2008/0269912 | A1 | 10/2008 | Gobbers |
| 2009/0036998 | A1 | 2/2009 | Finlinson |
| 2009/0132056 | A1 | 5/2009 | Kania |
| 2009/0157196 | A1 | 6/2009 | Danzig |
| 2009/0198346 | A1 | 8/2009 | Perkins et al. |
| 2009/0204229 | A1 | 8/2009 | Mosler |
| 2010/0087931 | A1 | 4/2010 | Bogue |
| 2010/0106260 | A1 | 4/2010 | Phillips |
| 2010/0262261 | A1 | 10/2010 | Laghi |
| 2010/0312359 | A1 | 12/2010 | Caspers |
| 2010/0312360 | A1 | 12/2010 | Caspers |
| 2011/0035027 | A1 | 2/2011 | McCarthy |
| 2011/0071649 | A1 | 3/2011 | McKinney |
| 2011/0130846 | A1 | 6/2011 | Kamapas |
| 2011/0202143 | A1 | 8/2011 | Caspers |
| 2011/0295386 | A1 | 12/2011 | Perkins et al. |
| 2012/0123559 | A1 | 5/2012 | Mosler et al. |
| 2012/0173000 | A1 | 7/2012 | Caspers |
| 2012/0173001 | A1 | 7/2012 | Caspers |
| 2012/0191217 | A1 | 7/2012 | Mackenzie |
| 2013/0053982 | A1 | 2/2013 | Halldorsson |
| 2013/0282142 | A1 | 10/2013 | Perkins et al. |
| 2013/0289741 | A1 | 10/2013 | Halldorsson et al. |

FOREIGN PATENT DOCUMENTS

| | | |
|---|---|---|
| CA | 2098945 | 7/1997 |
| DE | 745981 | 3/1943 |
| DE | 2712342 | 9/1977 |
| DE | 2729800 | 1/1979 |
| DE | 3221920 | 4/1983 |
| DE | 4217877 | 12/1992 |
| DE | 4321182 | 12/1994 |
| DE | 9418210.8 | 1/1995 |
| DE | 9419211.1 | 2/1995 |
| DE | 9417913.1 | 3/1995 |
| DE | 29905020 | 7/1999 |
| EP | 0019612 | 11/1980 |
| EP | 0057839 | 8/1982 |
| EP | 0057838 | 3/1985 |
| EP | 0086147 | 4/1987 |
| EP | 0261884 | 3/1988 |
| EP | 0320170 | 6/1989 |
| EP | 0363654 | 4/1990 |
| EP | 0631765 | 1/1995 |
| EP | 0650708 | 5/1995 |
| EP | 0870485 | 10/1998 |
| EP | 1509176 A1 | 3/2005 |
| EP | 1875881 A1 | 1/2008 |
| FR | 1135516 | 4/1957 |
| FR | 1532625 | 7/1968 |
| FR | 2420035 | 10/1979 |
| FR | 2501999 | 9/1982 |
| GB | 136504 | 8/1919 |
| GB | 267988 | 9/1925 |
| GB | 2069847 | 9/1981 |
| GB | 2149309 | 6/1985 |
| JP | 7-155343 | 6/1995 |
| SE | 88-01686 | 3/1989 |
| SU | 1667855 | 8/1991 |
| SU | 1771722 | 10/1992 |
| SU | 1812982 | 4/1993 |
| SU | 1821177 | 6/1993 |
| WO | 84/00881 | 3/1984 |
| WO | 95/05792 | 3/1995 |
| WO | 96/21405 | 7/1996 |
| WO | 98/04218 | 2/1998 |
| WO | 98/55055 | 12/1998 |
| WO | 9905991 A2 | 2/1999 |
| WO | 99/65434 | 12/1999 |
| WO | 00/03665 | 1/2000 |
| WO | 00/74611 | 12/2000 |
| WO | 01/54631 | 8/2001 |
| WO | 01/70147 | 9/2001 |
| WO | 02/26158 | 4/2002 |
| WO | 02/065958 | 8/2002 |
| WO | 02/067825 | 9/2002 |
| WO | 02067825 A2 | 9/2002 |
| WO | 02/080813 | 10/2002 |
| WO | 03/077797 | 9/2003 |
| WO | 03/099173 | 12/2003 |
| WO | 03/099188 | 12/2003 |
| WO | 2005039444 A2 | 5/2005 |
| WO | 2005/105000 | 11/2005 |
| WO | 2010/141960 | 12/2010 |
| WO | 2011/035099 | 3/2011 |

OTHER PUBLICATIONS

U.S. Appl. No. 11/956,034, filed Dec. 13, 2007, Caspers.
Brochure, "Sometimes Less is More, Harmony P3" Otto Bock, 12 pages. Available at, http://www.ottobock.com/cps/rde/xbcr/ob_es/646A303-EN-01-1001w.pdf, dated 2012.
Information Guide, "Harmony Users Guide Otto Bock, 9 pages, available at http://media.ottobock.com/Prosthetics/Socket-Technologies/Harmony/_Genreal/Files/12072403.1_OB-Harmony-UsersGuide-9-10-12.pdf", dated 2012.
Brochure,"Harmony Certification Course Manual,"Original Harmony Pump, 42 pages. Availiable at, http://academy.ottobockus.com/videos/harmony/data/downloads/harmony%20course%20manual%202013.pdf. Dated 2013.
Brochure, Harmony P2 & HD, 2 pages. Available at http://www.ottobock.com/cps/rde/xchg/ob_us_en/hs.xsl/14904.html?id=4641. Dated 2012.
International Search Report from corresponding PCT Application No. PCT/US2013/025849 dated Jun. 4, 2013.
Haberman, Louis J., "Silicone-Only Suspension (SOS) with Socket-Loc and the Ring for the Lower Limb", found at, http://www.oandp.org/jpo/library/1995_01_002.asp. Journal of Prosthetics and Orthotics 1995; vol. 7, No. 1, p. 2, 19 pages, dated 2012.
International Search Report and Written Opinion, App. No. PCT/US2013/038668, Aug. 7, 2013.

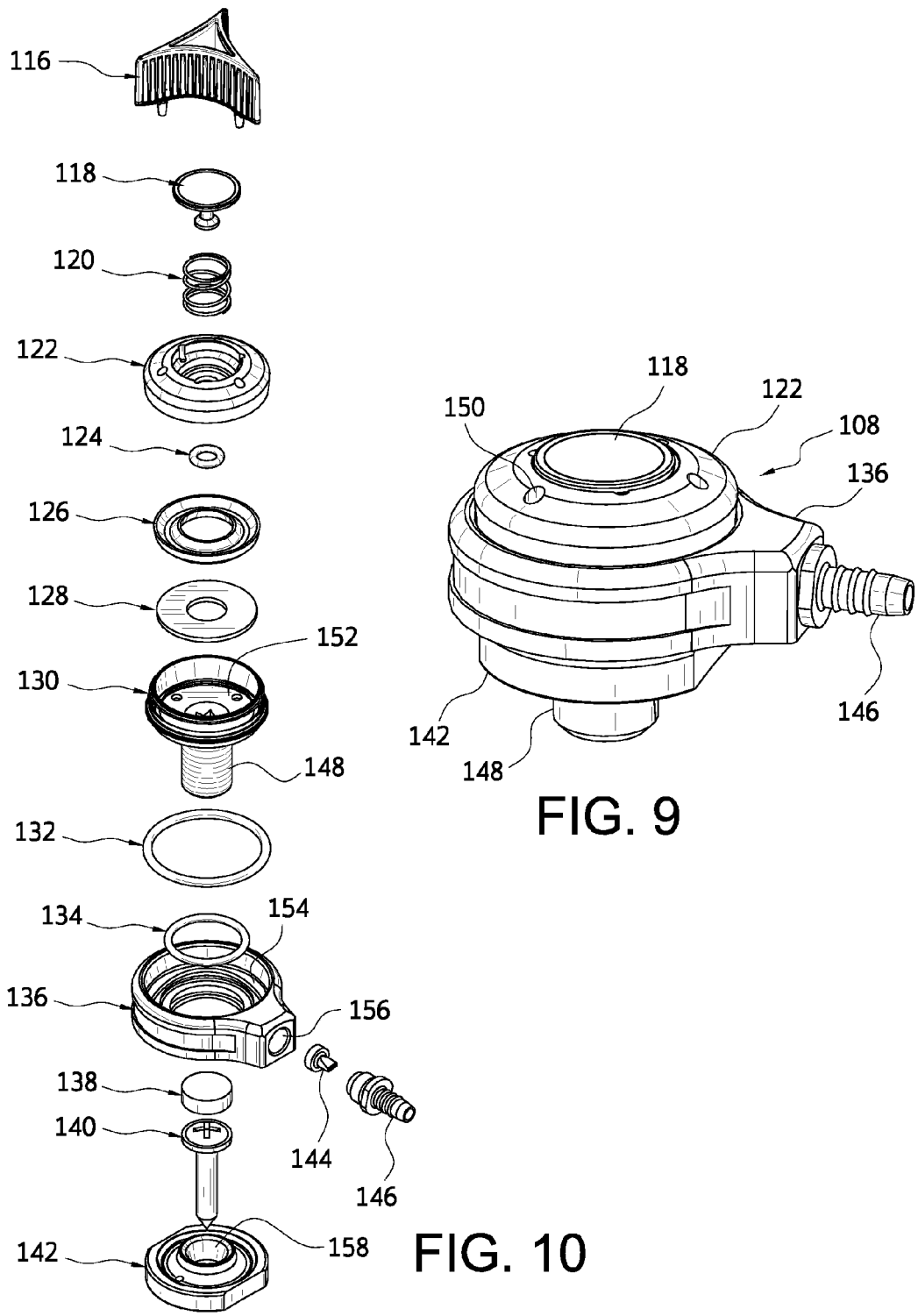

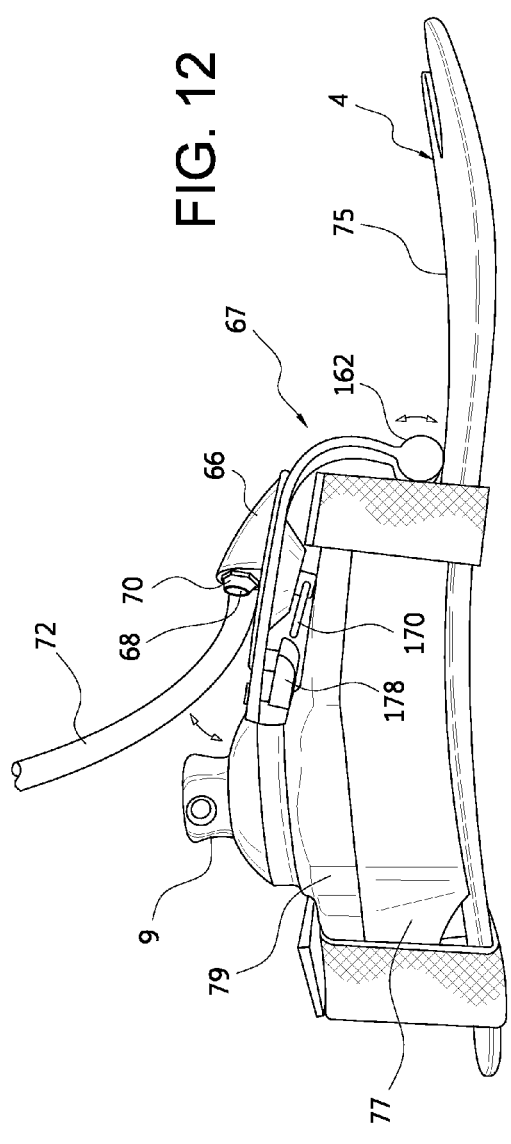
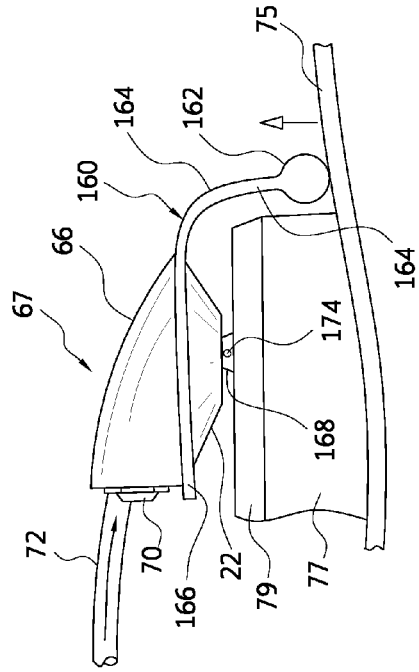
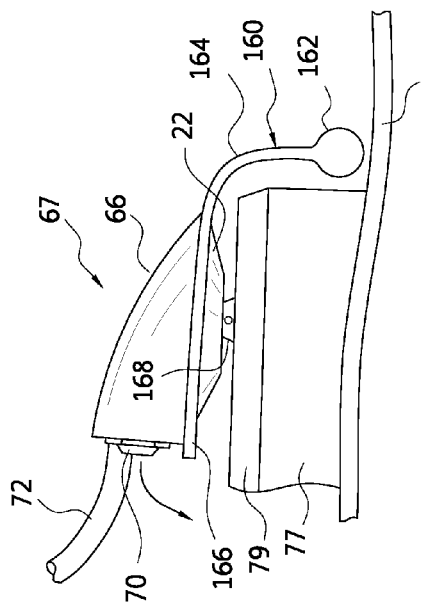

PROSTHETIC DEVICE, SYSTEM AND METHOD FOR INCREASING VACUUM ATTACHMENT

FIELD OF ART

The disclosure relates to the field of prosthetic devices, and more particularly to a prosthetic device, system and method for increasing vacuum in a vacuum assisted suspension system.

BACKGROUND

With advancements in prosthetic components, improved suspension solutions have become a pressing need. Elevated vacuum suspension has been around for nearly a decade, and improves proprioception and volume control. The concept is well accepted and has gained many users.

Many known elevated vacuum solutions on the market rely solely on sleeves or reflecting liners for placement over a socket to achieve an airtight seal necessary for an effective vacuum. This mode of sealing, particularly sleeves, adds to material thickness over the knee and constrains knee bending dramatically for trans-tibial amputees.

A vacuum in the sense of elevated vacuum solutions refers to creating pressure significantly lower than atmospheric pressure. In prosthetic systems, a vacuum is not applied directly to the skin, but typically between the hard socket and the skin interface. The vacuum system is adapted to stabilize soft tissue volume at the residuum that the liner and hard socket surround and maintain more effective suspension of a prosthetic system.

A significant drawback to known elevated vacuum solutions is they fail to adapt to limb volume change which occurs particularly when a user is walking. Yet another drawback is that many known systems have a tendency to lose suction due to the method used to seal the socket and hence the vacuum formed. Many of such vacuum systems are bulky and significantly contribute to the weight of the prosthetic device, wherein the hard socket may be oversized to accommodate vacuum chambers, or additional attachments are used to supply or assist in vacuum generation.

In sleeve based systems, a sleeve is applied at the proximal end of the hard socket and the vacuum is often formed along the entirety or near entirety of residual limb covered by the hard socket. The vacuum is formed along the length of the covered residual (i.e., "above-knee" vacuum systems) and does not account for areas of the residual limb more or less prone to volume change. When the sleeve is removed, the seal is broken and the vacuum is lost. While valves may be used in combination with vacuum suspension, these solutions often lack means to quickly release the vacuum.

There is a need for a prosthetic device, system and method that provides freedom of vacuum suspension for a prosthetic system with no sleeve. There is also a call to provide a prosthetic device, system and method to minimize changes in the volume of a residual limb with vacuum suspension, providing secure vacuum without losing suction and confidence to the user over a period of use. There is a demand for applying a vacuum where it is needed, while still stabilizing volume and maintaining vacuum suspension. It is desirable for prosthetic devices to draw a vacuum while being lightweight and streamlined.

SUMMARY

Embodiments of the prosthetic device, system and method provide the security and freedom of vacuum suspension without the sensation and restrictions of a sleeve, or the accompanying bulk and complicated features and attachments. Without a sleeve, range-of-motion can be less restricted and the vacuum can be released quickly and easily by a release valve.

The embodiments address volume fluctuation for effective volume stabilization. The embodiments have a capacity to create a distal vacuum and stabilize soft tissue volume and maintain effective suspension. By locating distal suspension, the embodiments avoid the risk of proximal vacuum leakage and any puncture issues that may arise with full vacuum systems.

The embodiments are preferably but not limited to forming a distal vacuum around the distal part of the limb to stabilize volume while creating effective and sleeveless vacuum suspension. The embodiments rely on the understanding that the distal end of the limb, where there is typically more soft tissue, is the area most susceptible to volume fluctuations and the area which requires efficient stabilization to maintain good suspension and prosthetic function. The area closer to the knee containing bones and tendons is relatively stable over the day and do not fluctuate significantly in volume, thereby removing the necessity for negative pressure to be formed throughout the entirety of the prosthetic socket.

The embodiments comprise a mechanical vacuum pump or mechanism providing vacuum assisted suspension by generating negative pressure inside a prosthetic socket worn over a residual limb, and reducing sliding movement between the liner and the socket. The function of the embodiments is automatic as it is activated during gait; the weight placed on the heel of a prosthetic foot expands the vacuum pump which efficiently draws air out from the socket in each step, and expels it into the atmosphere during swing phase as the reservoir compresses again. The pump mechanism creates a negative pressure inside the socket, resulting in secure and reliable elevated vacuum suspension. The vacuum assisted suspension enables intimate suspension as the negative pressure formed inside the socket holds the liner and residuum firmly against the socket wall.

According to an embodiment, a prosthetic system has a prosthetic foot, a pump mechanism defining first and second sides, a first member connected to the prosthetic foot and the first side of the pump mechanism, and a second member carrying the pump mechanism and engaging the prosthetic foot. The second side of the pump mechanism is connected to the second member. The first and second members are movable relative to one another upon movement of the prosthetic foot such that the pump mechanism varies in volume as the first and second members move relative to one another.

The prosthetic system includes a prosthetic socket in fluid communication with the pump mechanism and connected to the prosthetic foot. A tube connects an interior of the prosthetic socket to a first port of the pump mechanism. The pump mechanism is arranged to draw air from the prosthetic socket interior upon expansion of the pump mechanism. The pump mechanism has a second port including a one-way valve arranged for expelling air drawn from the prosthetic socket interior.

A suspension liner has a seal component adapted to engage at least an interior wall of the prosthetic socket. The seal component is located on a distal end of the suspension liner and circumferentially engages the interior wall of the prosthetic socket defining an interior of the prosthetic socket. The area distally below the seal component forms a vacuum zone within the prosthetic socket. The tube connects the prosthetic socket interior within the vacuum zone to the first port of the pump mechanism.

A valve may be secured to the socket and connect the prosthetic socket interior to the tube. The valve is arranged to permit expulsion, vacuum bypass and vacuum release.

A second end of the first member is secured to the second member, and the first member has a first end secured to the prosthetic foot, and a second end extending freely over a surface of the prosthetic foot. A compressible heel element may be connected to the second member and extend between upper and lower sections of the prosthetic foot.

According to the embodiments of the prosthetic system, a method for using the embodiments provides vacuum suspension. The method may include the steps of locating the seal component at a distal area of the suspension liner, forming a vacuum zone at a distal area of the prosthetic socket from the seal component to the distal end of the prosthetic socket, connecting the pump mechanism to the vacuum zone, and articulating the prosthetic foot to actuate the pump mechanism to draw a vacuum from the vacuum zone during gait of a user.

The method may further comprise the steps of connecting the pump mechanism to the prosthetic socket via a tube arranged for drawing a vacuum from the interior of the prosthetic socket and through a first port on the pump mechanism depending on movement of the prosthetic foot during gait, and expelling air drawn by the pump mechanism through a second port on the pump mechanism on movement of the prosthetic foot during gait.

In another embodiment, a prosthetic device is arranged for securing to a prosthetic foot. The prosthetic device includes a pump mechanism defining first and second sides, a first member arranged for securing to a prosthetic foot and connected to the first side of the pump mechanism, and a second member carrying the pump mechanism and engaging the prosthetic foot. The second side of the pump mechanism is connected to the second member. The first and second members are movable relative to one another upon movement of the prosthetic foot such that the pump mechanism varies in volume as the first and second members move relative to one another.

The pump mechanism includes first and second ports, where the first port is arranged to draw fluid due to the increase of volume of the membrane, and the second port includes a one-way valve is adapted to expel fluid upon relaxation of the membrane.

The first side of the pump mechanism may be pivotally coupled to the first member.

A compressible heel element may be securable to a prosthetic foot, and the first member extends over the heel element. A connector secures to a first side of the pump mechanism to the first member.

In an embodiment of the pump mechanism, it may include a housing having first and second ports, a fluid chamber with a volume defined by an enclosure at least partially formed from a flexible material where an upper side of the fluid chamber is in fluid communication with the first and second ports, and a connector connected to a lower side of the enclosure. A portion of the enclosure is shifted to increase the volume of the fluid chamber.

The pump mechanism may include a tube connected to the first port. The first port is arranged to draw fluid through the tube due to the increase of volume of the fluid chamber. The second port may include a one-way valve. The increase in the volume of the fluid chamber preferably occurs by deforming or extending a wall of the enclosure.

The enclosure may have two opposing walls connected by at least one side wall. The connector is formed of an insert attached to the enclosure, and may include a fastener securing to the insert. In an alternative embodiment, the connector has a pivotable coupling part.

In a variation, the housing includes an arm section having first and second ends, a plate section extending from the first end of the arm section, and a bumper secured to a second end of the arm section. The first and second ports are located over the plate section of the housing. The bumper may include a roller element.

The pump mechanism may be combined in a prosthetic system including a prosthetic component. The pump mechanism includes a connector connected to a lower side of the enclosure and the prosthetic component, such that a portion of the enclosure is shifted due to movement of the prosthetic component to increase the volume of the fluid chamber.

The prosthetic component may be a prosthetic foot. In an embodiment, a first member connects the pump mechanism to a portion of the prosthetic foot. The first member has an extending section movable relative to the prosthetic foot such that when weight of a user is applied to the prosthetic foot causing motion of the member, a portion of the enclosure is shifted to increase the volume of the fluid chamber. The first member may secure to a proximal end of the prosthetic foot, and the extending section extends freely over at least an ankle portion of a front surface of the prosthetic foot.

The embodiment may include a second member connected to the first member and extending thereover. The pump mechanism is preferably mounted to the second member and the connector mounted to the first member. The fluid chamber changes in volume between the first and second members upon action of the prosthetic foot.

According to a variation, the housing of the pump mechanism further includes an arm section having first and second ends, a plate section extending from the first end of the arm section, and a bumper secured to a second end of the arm section. The bumper is arranged to engage the prosthetic foot.

Embodiments of the disclosure are preferably arranged to apply an elevated vacuum with a sealing suspension liner, for example a seal component extending from the suspension and arranged to engage an inner wall of a socket. The embodiments preferably employ a single pump mechanism mounted on and having minimal impact on the function of a prosthetic foot.

BRIEF DESCRIPTION OF THE DRAWINGS

The prosthetic device is described referring to the accompanying drawings which show preferred embodiments according to the device described. The device, system and method as disclosed in the accompanying drawings are illustrated for example only. The elements and combinations of elements described below and illustrated in the drawings can be arranged and organized differently to result in embodiments still within the spirit and scope of the device described.

FIG. 9 is a perspective view of a tri-function valve in the vacuum suspension system of FIG. 8.

FIG. 10 is an exploded view of the tri-function valve of FIG. 9.

FIG. 12 is another embodiment of the prosthetic device.

FIG. 13A is a sectional view of the pump mechanism in FIG. 12 in a first configuration of the prosthetic foot.

FIG. 13B is a sectional view of the pump mechanism in FIG. 12 in a second configuration of the prosthetic foot.

DETAILED DESCRIPTION OF VARIOUS EMBODIMENTS

Figure 1:
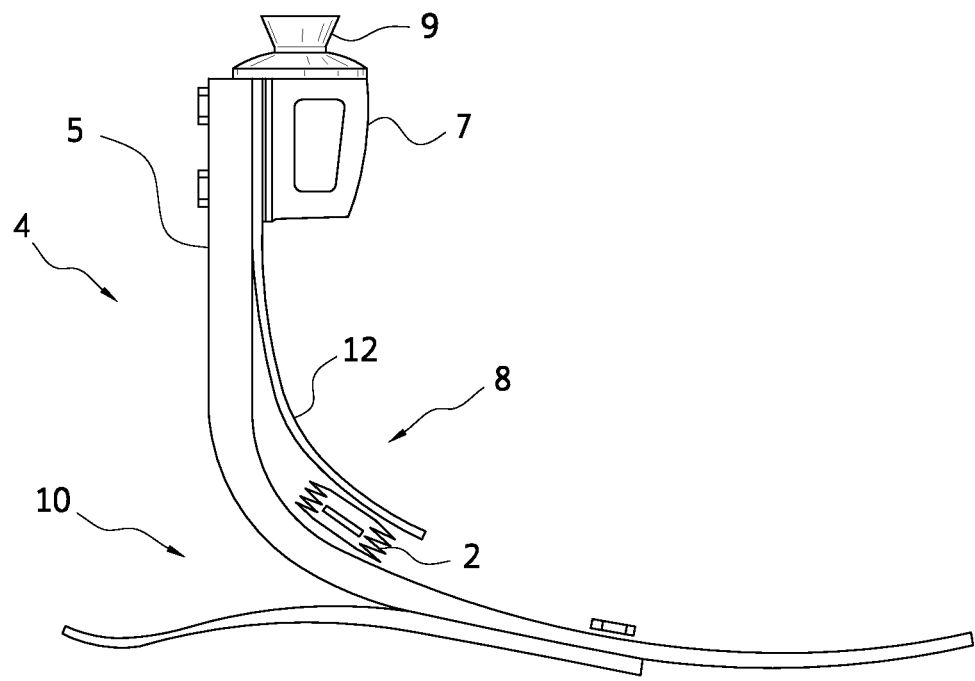
FIG. 1 shows a side view of an embodiment of the prosthetic device.

A better understanding of different embodiments of the prosthetic device may be gained from the following description read with the accompanying drawings in which like reference characters refer to like elements.

While the disclosure is susceptible to various modifications and alternative constructions, certain illustrative embodiments are in the drawings and will be described below. It should be understood, however, there is no intention to limit the disclosure to the specific embodiments disclosed, but on the contrary, the intention covers all modifications, alternative constructions, combinations, and equivalents falling within the spirit and scope of the disclosure and defined by the appended claims.

It will be understood that, unless a term is expressly defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

The embodiments of a prosthetic device will be described which form part of a vacuum system. A vacuum pump mechanism having a fluid connection with a socket assists in creating a vacuum between a residual limb and the socket by pumping fluid out of the socket. The fluid is pumped out of the socket when the user puts his weight on a prosthetic foot such as upon a heel strike. The compressive force of the heel strike causes the pump to increase the volume of a fluid chamber in the pump. The increase in volume of the pump draws in fluid from the vacuum space between the residual limb and the socket of a prosthetic limb. In this manner, the pump decreases the air pressure within the vacuum space causing a vacuum effect.

After the compressive force is removed during toe-off and the swing phase of gait, the volume of the fluid chamber in the pump is decreased. The connection between the vacuum space and the pump may have a one-way valve, so all of the air within the volume of the pump is expelled out of an outlet to another space or to atmosphere. The outlet is provided with a one-way valve so the vacuum space is the only source of air.

This method of producing a vacuum effect in the prosthetic socket is advantageous over prior methods of compressing the pump to expel air and decompressing the pump to draw in air. The method described achieves smaller fluctuations in air pressure than the prior method, so the difference between the greatest pressure and lowest pressure in the vacuum space is less in the method described compared to the prior method.

The efficiency of the pump is determined partially by how effectively the volume of the fluid chamber is reduced. Since the pump returns to the original state of zero or near-zero volume at the beginning or end of each cycle, the volume of the fluid chamber is determined by the compressive force applied to the pump. In the method described, all fluid drawn into the pump is expelled afterwards fully utilizing each cycle. The method described may be implemented using a pump that has no spring type elements which may affect the bio-mechanical function of the prosthetic device.

In the prior methods, the system relies on a complete compression of the pump in expelling air in each cycle to use the pump to its maximum capacity. It is difficult for complete compression to occur in every cycle using the gait of a user as the compressive force since the impact and displacement of the pump is not consistent and varies between users.

The vacuum suspension system also reduces volume fluctuations of the residual limb and allows for increased proprioception and reduced pistoning since there is a better attachment between the socket and the residual limb. It may also be beneficial to produce hypobaric pressure below a certain level in the socket. This may be achieved using a sealing membrane or seal component between the residual limb and the socket, instead of the conventional sealing method of using a sleeve to form an airtight connection between the residual limb and the proximal end of the socket. The sealing membrane may be on a prosthetic liner as described in U.S. Pat. No. 8,034,120 incorporated by reference and belonging to the assignee of this disclosure.

The benefit of using a liner having a seal or seal component reduces the volume of air to be drawn out of the socket and therefore, a better suspension may be achieved in a shorter time period. Using a silicone liner with integrated seal also provides the added benefit that the hypobaric region is not directly applied to the skin.

The vacuum pump mechanisms in the embodiments of the prosthetic device described are generally described as a pump mechanism. A bladder-type pump may be used in the embodiments in place of a membrane-type pump, and a skilled person would understand that the pump mechanisms described may also be used with a bladder-type pump and vice versa.

A bladder-type pump has an interior fluid chamber surrounded by an airtight material. When the interior chamber is expanded, the opposing walls are moved away from each other by extending at least one side wall of the pump. The side walls of the bladder-type pump may have an accordion-like shape or be formed of a polymeric material which allow for the increase in distance between the opposing walls.

A membrane-type pump has at least one wall of flexible material and a second opposing wall which may be rigid or flexible. The edges of the two walls are attached to each other such that when a force applies to the pump to expand the interior fluid chamber, the force deforms at least the flexible wall, and the flexible wall arcs outward to form an interior fluid chamber. To allow for deformation, the flexible wall may be made of a polymeric material including elastomeric material such as rubber or plastic.

The bladder-type pump and membrane-type pump are arranged so that when no force applies to the pump or no weight is placed on the prosthetic device the volume of the interior fluid chamber is zero or near-zero. The pumps described and shown have a cylindrical shape. A skilled person would understand that the pumps may have a variety of shapes, for example, a diamond, rectangular, or triangular shape.

The specific embodiments of the prosthetic device will now be described regarding the figures.

First Embodiment of the Prosthetic Device

FIG. 1 shows a first embodiment of the prosthetic device comprising a pump mechanism 2 and a prosthetic foot 4. The pump mechanism 2 has two opposing walls and at least one side wall. The prosthetic foot 4 has an ankle area 8, a heel area 10, and a movable member 12 attached at one end to the prosthetic foot 4 and extending over the front of the prosthetic foot 4 leaving an unattached end. The attached end of the moveable member 12 may be pivoting or non-pivoting. The moveable member 12 generally follows the curvature of the front of the prosthetic foot 4 and a clearance between the moveable member 12 and the front of the prosthetic foot 4 gradually increases. The pump mechanism 2 is placed in the clearance between the movable member 12 and the front of the prosthetic foot 4 within the ankle area 8 near the unattached end of the moveable member 12. One side of the pump is attached to the member 12 and another side of the pump is attached to the prosthetic foot 4.

The pump mechanism 2 may be a bladder-type pump or a membrane-type pump as discussed above. FIG. 1 shows the pump mechanism 2 as being a bladder-type pump. The bladder-type pump may be formed of an elastomeric material such that the walls of the pump mechanism 2 can stretch when opposing forces apply to the opposing walls of the pump mechanism 2.

When a user steps, such as a heel strike, weight is placed on the heel of the foot 4 and the moveable member 12 moves away from the foot 4 pulling the attached wall and causing the volume of the internal fluid chamber of the pump mechanism 2 to increase. The increase in volume of the fluid chamber draws fluid into the interior fluid chamber. During the stance phase or toe-off, the moveable member 12 compresses the pump mechanism 2 decreasing the volume of the internal chamber and causing the pump mechanism 2 to expel fluid within the fluid chamber. The pump mechanism 2 may be fitted with one-way valves to control the direction of fluid flow so that fluid is not drawn from the atmosphere when the volume of the internal chamber is increased, and the fluid is not expelled into the socket when the pump mechanism 2 is compressed.

Figure 2:
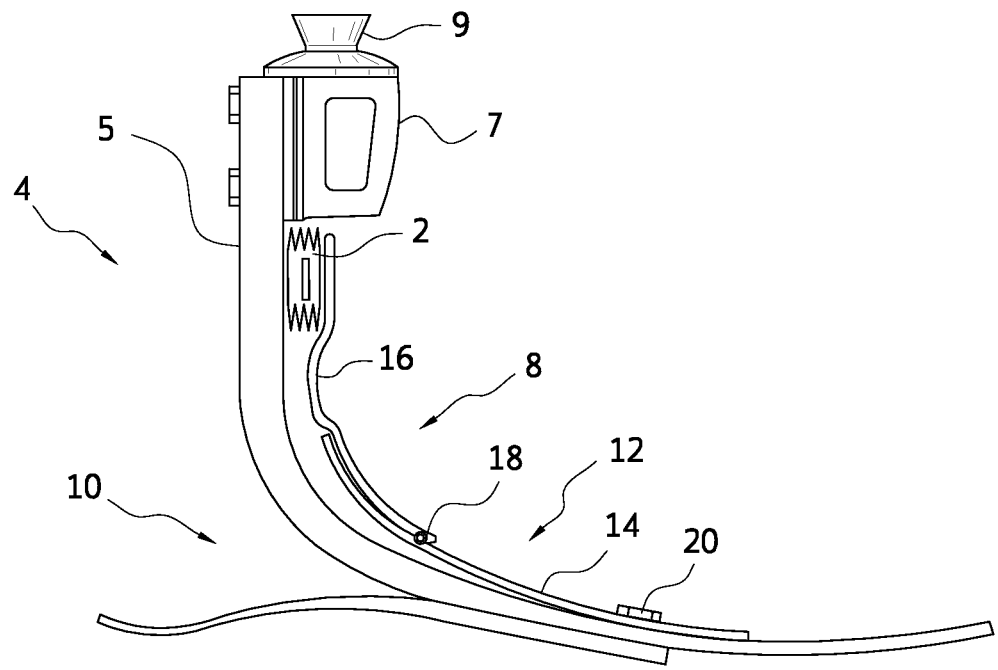
FIG. 2 shows a side view of another embodiment of the prosthetic device.

The vacuum pump mechanism 2 can be placed in various areas of the prosthetic foot 4 along the front of the foot. As shown in FIG. 2, the movable member 12 may be attached to the shin of the prosthetic foot 4 and extend towards the pylon attachment point of the prosthetic foot 4. The moveable wall 12 is attached using a common foot attachment 20. The vacuum pump mechanism 2 is similarly placed near the unattached end of the moveable member 12. In an embodiment as shown in FIG. 2, the moveable member 12 comprises a first piece 14 and a second piece 16 connected at a non-pivoting joint 18. Using two pieces 14, 16 provides a greater overall range of distances between the wall and the prosthetic foot at the open end.

The moveable member 12 and pieces 14, 16 may be formed of many materials including carbon fiber, plastic, and metal. The moveable member 12 may take a variety of forms including a plate, wire, or arm.

In this embodiment, as used in others, the moveable member 12 connects to the proximal end 5 of the prosthetic foot 4, whereat a connector 7 carries a male pyramid adapter 9.

Second Embodiment of the Prosthetic Device

Figure 3:
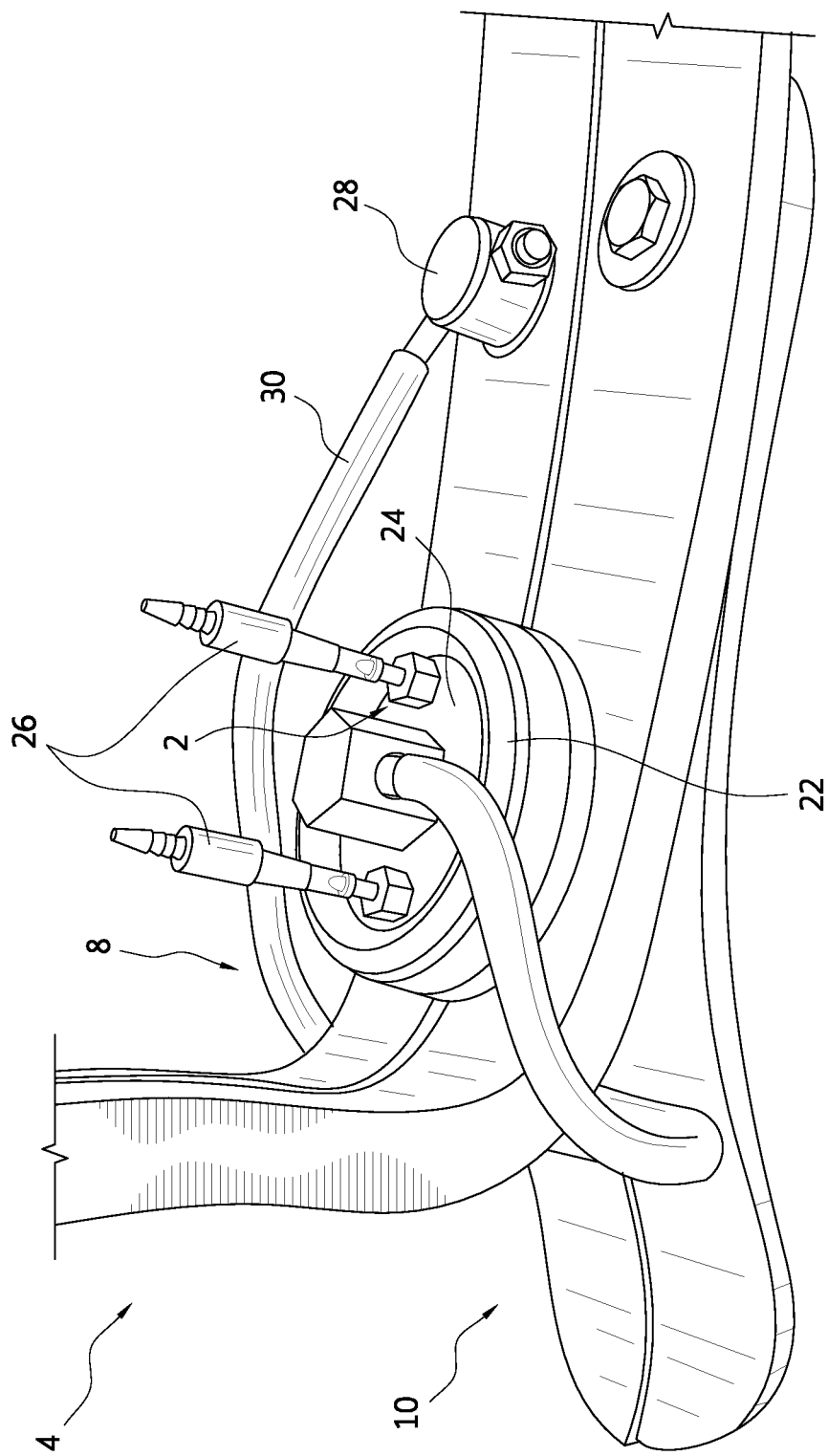
FIG. 3 shows an embodiment of the prosthetic device with a pump mechanism.

FIG. 3 shows another embodiment of the prosthetic device comprising a vacuum pump mechanism 2 and a prosthetic foot 4. The vacuum pump mechanism 2 in this embodiment is a membrane-type pump comprising a flexible membrane 22 and a rigid wall 24. The flexible membrane 22 forms a seal with the rigid wall 24. In FIG. 3, this seal may be formed by having the flexible membrane 22 extend over and around the edges of the rigid wall 24 such that the rigid wall 24 fits within a recess formed by the edges of the flexible membrane 22. An airtight seal between the rigid wall 24 and the edges of the flexible membrane 22 may be formed using an adhesive.

A moveable member 30 is attached at one end to the prosthetic foot 4 in the midfoot area with a pivoting attachment 28, and the moveable member 30 wraps around the heel area 10 of the foot 4. The portion of the moveable member 30 located within the heel area 10 maintains contact with the heel portion of the foot 4 such that on a heel strike the heel portion of the foot 4 rotates the arm upward and pulls the rigid wall 24 causing a deformation of the flexible membrane 22. Simultaneous to the upward movement of the moveable member 30, the ankle portion of the foot 4 moves downwards.

The total deformation of the flexible membrane 22 combines the displacement of the rigid wall 24 caused by the upward movement of the moveable member 30 and the downward movement of the ankle portion to which the flexible membrane 22 is attached. The flexible membrane 22 and rigid wall 24 are simultaneously pulled away from each other, and the displacement between the bottom of the flexible membrane 22 and the rigid wall 24 corresponds to the displacement between ankle and heel portions of the prosthetic foot 4.

During displacement of the flexible membrane 22 and the rigid wall 24, a fluid chamber is formed or the volume of an existing fluid chamber is increased to draw in air through a one-way valve 26 by deforming the flexible membrane 22. In the embodiment in FIG. 3, the flexible membrane 22 has a circular shape and is attached to the prosthetic foot at its center point while the edges of the flexible membrane 22 are firmly attached to the rigid wall such that when the flexible membrane 22 and rigid wall 24 are pulled away from each other a pocket forms in the middle of the flexible membrane due to the deformation of the flexible membrane 22.

Once weight is removed from the heel portion of the prosthetic foot 4, the flexible membrane 22 and rigid wall 24 move towards each other and fluid within the fluid chamber is expelled out of a one-way valve 26.

Third Embodiment of the Prosthetic Device

FIG. 4 shows another embodiment of the prosthetic device having a prosthetic foot 4 and a membrane-type vacuum pump mechanism 2. The moveable member 30 in this embodiment is formed as a combination of two moveable plates 32, 34. The top plate 32 is connected to the rigid wall 24 and, in FIG. 4, is shown as extending through the rigid wall 24. The bottom plate 34 is connected to the flexible membrane 22 near the membrane's attachment point 40 to the prosthetic foot 4. The bottom plate 34 is also attached to the front of the prosthetic foot 4 in the shin area of the foot 4. The bottom plate 34 follows the curve of the foot 4 by having a substantially constant clearance between the bottom plate 34 and the foot 4. Near the midfoot and forefoot areas, the clearance between the bottom plate 34 and the foot 4 increases so the bottom plate 34 does not impede the gait of the user.

The top plate 32 is present between the ankle area and the midfoot area of the foot 4 and is partially parallel to the bottom plate 34. The top plate 32 and the bottom plate 34 meet in the midfoot area and form a firm connection at a common attachment point. The top plate 32 has two arms 42 which extend down each side of the foot 4 from the top plate 32 to the heel area of the prosthetic foot 4. A heel cylinder 36 is connected between the arms 42 and rests on the heel of the foot 4.

Similar to a previous embodiment, the vacuum pump mechanism 2 in the embodiment in FIG. 4 utilizes the displacement which occurs between the ankle area and the heel area of the foot during a heel strike to increase the volume of the fluid chamber within the vacuum pump mechanism 2. When the heel strikes the ground, the heel of the foot 4 presses on the heel cylinder 36 and causes the top plate 32 and rigid wall 24 to shift away from the front of the prosthetic foot 4. The ankle of the foot 4 is depressed causing the membrane fixed to the rigid wall 24 and the foot 4 to be deformed expanding the fluid chamber within the pump mechanism 2.

The pump mechanism 2 can be arranged at a variety of points on the front of the prosthetic foot in combination with different angles of the arms 42 to maximize the length of the displacement between the stationary position of the pump and compressed position.

The membrane used in the embodiments described can vary in thickness in different areas and in shape. The thickness of the membrane may be thicker at the portions attached to the rigid wall to create a stronger connection and greater deformation of the membrane wall. Similarly, the membrane wall may be thinner than the attachment portions to allow for greater displacement with less force. The membrane may a cylindrical shape or a tapered shape as shown in FIG. 4B.

Fourth Embodiment of the Prosthetic Device

Figure 5A:
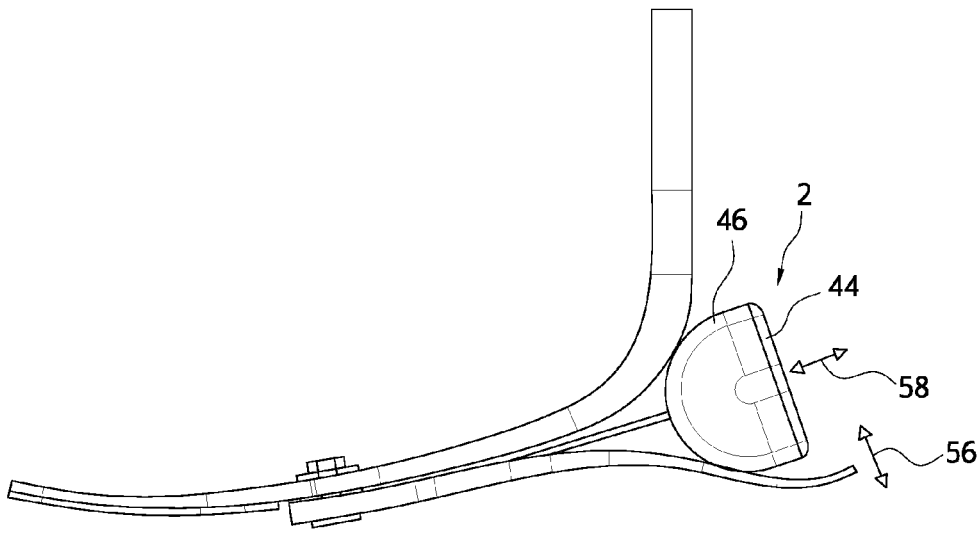
FIG. 5A shows another embodiment of the prosthetic device which compresses a housing of a vacuum pump to actuate the pump.
Figure 5B:
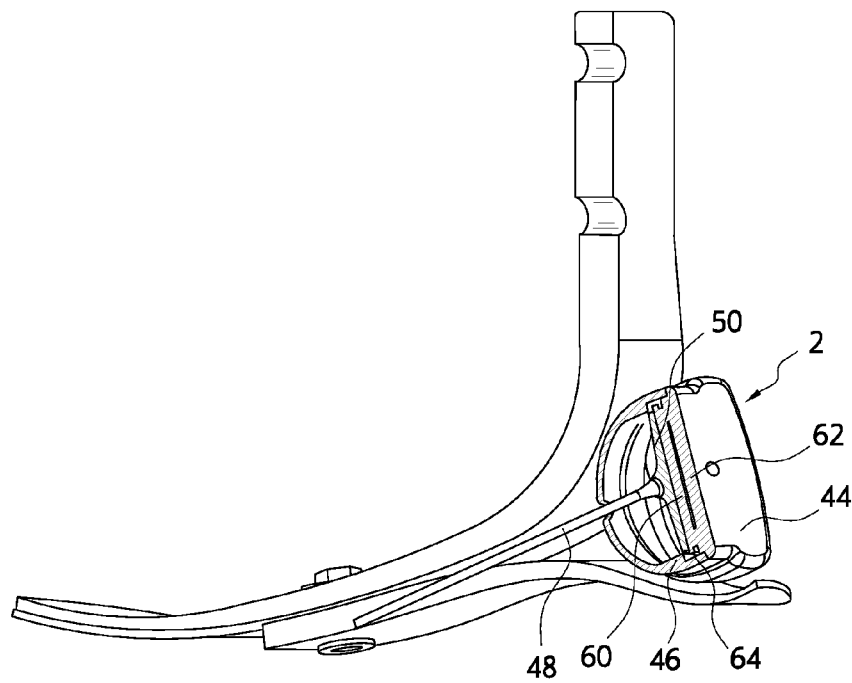
FIG. 5B shows a cross-section of the embodiment in FIG. 5A.

FIGS. 5A and 5B depict another embodiment of the prosthetic device. FIG. 5A is a side view of the prosthetic device, and FIG. 5B is a cross-section of the embodiment in FIG. 5A.

The pump mechanism 2 in FIG. 5A comprises a flexible enclosure 44 and a housing 46. The housing 46 has a semicircular shape having an open end. The interior wall of the housing 46 along the open end has an indentation for receiving the flexible enclosure 44, and the flexible enclosure 44 forms a covering for the open end. The exterior wall of the flexible enclosure 44 is attached to the housing 46. An anchor member 48 extending from the foot 4 through the housing 46 attaches to the other side of the flexible enclosure 44.

Upon a heel strike, the interior wall is deformed due to stress placed on the edges of the interior wall and an interior fluid chamber is formed or expanded. The ankle and heel of the foot 4 compress the housing 46 and shift the housing 46 outwards which causes the housing 46 to push the edges of the flexible enclosure 44 outwards. Meanwhile, the anchor member 48 is firmly attached to the interior enclosure wall, preferably near the center of the interior enclosure wall, and since the interior enclosure wall remains stationary, the outward movement of housing 46 causes at least the interior wall to deform and increase the volume of an interior fluid chamber.

The compressive force on the housing 46 is provided along a first axis 56, and the resulting expansion of the fluid chamber is along a second axis 58 substantially perpendicular to the first axis 56.

The anchor member 48 preferably ends with an arm plate 50 attached to the interior enclosure wall. The arm plate 50 is semi-rigid so that once the compressive force is removed from the housing 46, the housing 46 and the flexible enclosure 44 return to their unextended state which causes the fluid drawn into the interior fluid chamber to be expelled.

The anchor member 48 may be attached to the interior wall using hooks or adhesive or some other form of mechanical connection. The arm plate 50 may be provided with hooks which attached to the interior wall of the enclosure 44. The hooks may also fit within a groove along the interior circumference of the wall such that when the housing shifts outward the hooks remain in the groove causing the attachment point of the wall to remain stationary while the edges around the interior wall shift outward.

In another embodiment, the enclosure 44 is formed of two separate opposing walls. The opposing walls are attached to each other using a mechanical connection such as a screw. A seal is formed between the opposing walls through the strength of the mechanical connection.

The flexible enclosure 44 is described as operating as a membrane-type pump, and a skilled person would understand that the flexible enclosure 44 may also be in a bladder-type pump having a reciprocating wall.

Fifth Embodiment of the Prosthetic Device

Figure 6:
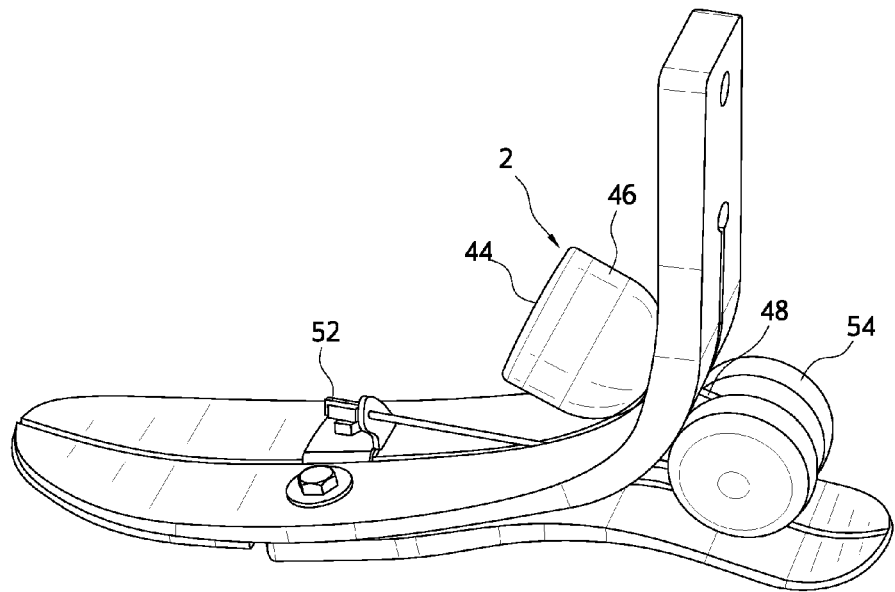
FIG. 6 shows an embodiment of the prosthetic device having a cylinder block in the heel area of a prosthetic foot.

FIG. 6 shows an embodiment of the prosthetic device using the pump mechanism 2 of the embodiment in FIGS. 5A and 5B. In the embodiment of FIG. 6, the pump mechanism 2 is attached on the front of the prosthetic foot 4 in the ankle area of the foot 4. The anchor member 48 wraps around a cylindrical block 52 and through the foot 4 to connect to the pump mechanism 2.

In this embodiment, the housing 46 remains stationary while the cylindrical block 52 is pushed outwards when weight applies to the heel of the foot 4. The interior flexible enclosure wall is pulled due to a pulley effect create by the outward movement of the cylindrical block 52 on the anchor member 48 to which the interior wall is attached. When the anchor member is pulled outwards, the interior wall flexes or deforms starting at the attachment point of the interior wall and the anchor member to cause the interior fluid chamber to expand. For an embodiment using a bladder pump, the interior wall may reciprocate within the housing.

The anchor member may be a cable or wire made of a flexible material such as an elastomeric material, metal, or plastic.

Sixth Embodiment of the Prosthetic Device

Figure 4A:
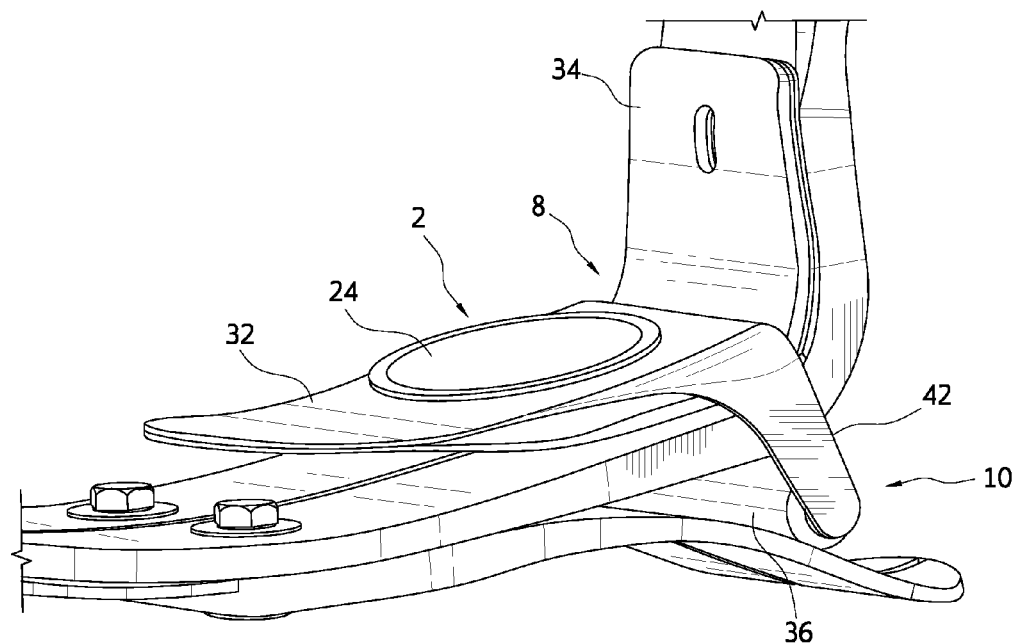
FIG. 4A shows a view of an embodiment of the prosthetic device having two plates from the front.
Figure 4B:
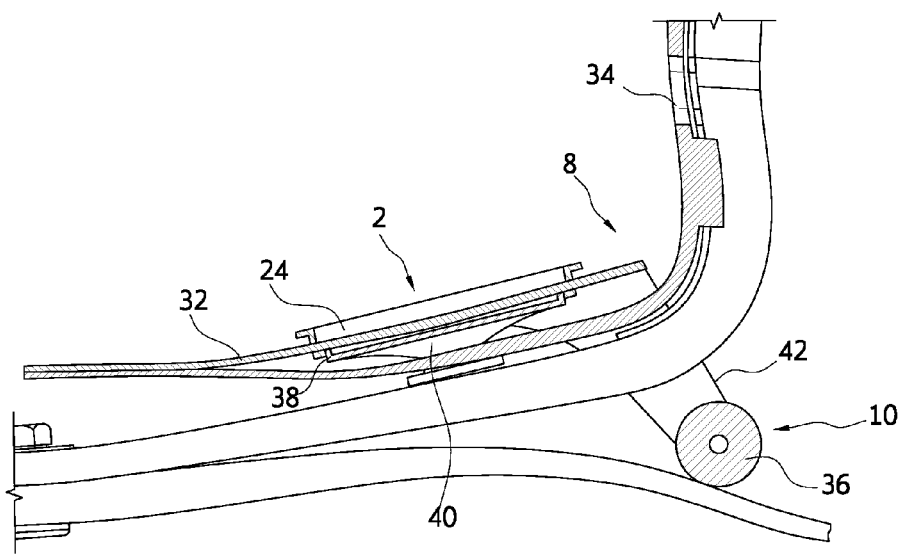
FIG. 4B shows a cross-section of the embodiment in FIG. 4A.
Figure 7A:
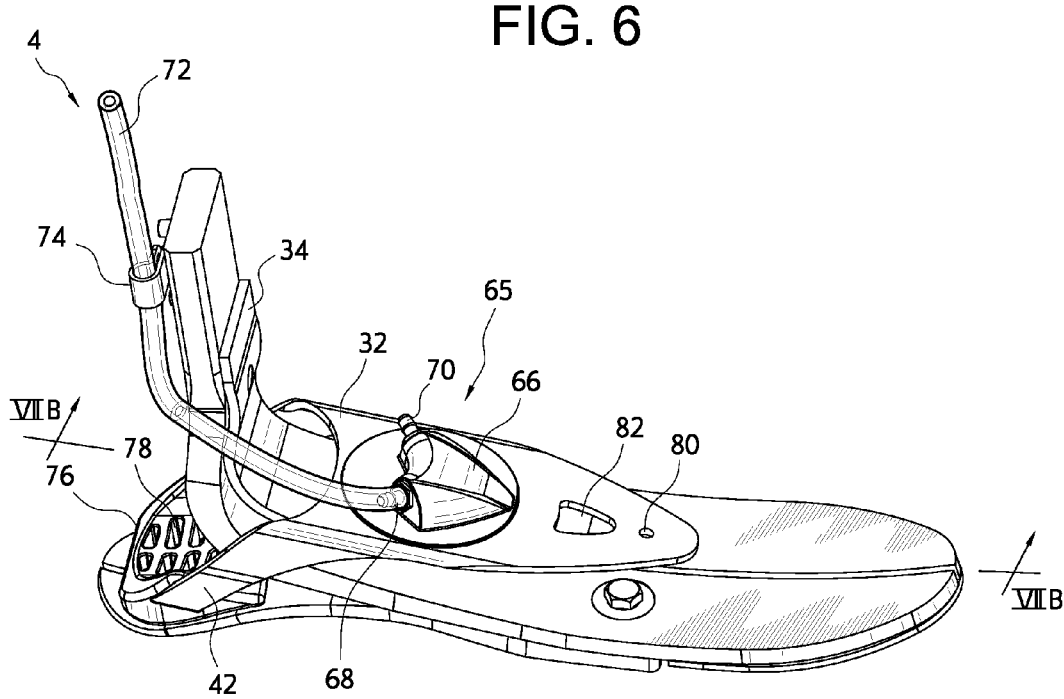
FIG. 7A shows another embodiment of the prosthetic device.
Figure 7B:
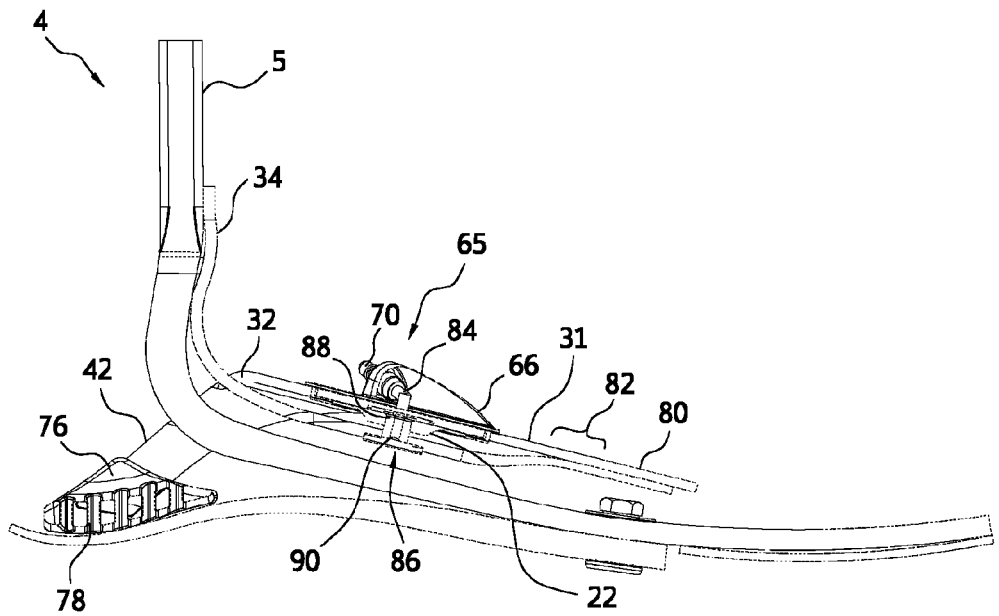
FIG. 7B is a cross-sectional side view along line VIIB-VIIB of the embodiment shown in FIG. 7A.
Figure 7C:
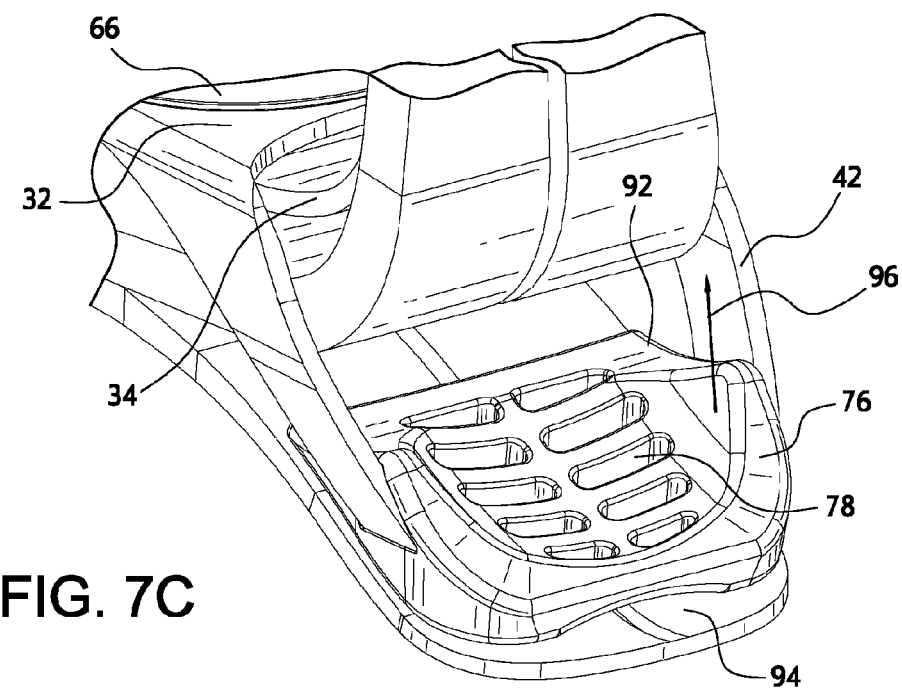
FIG. 7C is a detailed view of the heel element of the embodiment shown in FIG. 7A.

The sixth embodiment of the prosthetic device in FIGS. 7A-7C is similar to the third embodiment illustrated in FIGS. 4A and 4B. Elements similar between these embodiments are identified with the same reference numerals.

The prosthetic foot 4 has a vacuum pump mechanism 65 attached to the foot 4 through two plates 32, 34. The pump mechanism 65 is placed on a top surface of top plate 32 and operable between the two plates as shown in more detail in FIG. 7B. The pump mechanism 65 has a housing 66 containing two one-way valves 68, 70, a membrane 22, and a membrane connector 86. The valve 68 only allows fluid to enter the pump mechanism 65 and is connected to a tube 72. Through the tube 72, the pump mechanism 65 is in fluid communication with the cavity of the prosthetic socket. The tube 72 may be secured to the foot 4 with a tube attachment 74. The other valve 70 only allows fluid to be expelled out of the pump mechanism 65 preferably to atmosphere.

Similar to the third embodiment, upon a heel strike, the force on the heel of the foot 4 and a heel element 76 in the direction of arrow 96 in FIG. 7C relative to the foot flexes causes the top plate 32 to flex near the anterior end portion of the top plate 32 to pull the housing 66 away from the membrane 22. When the housing 66 attached to the top plate 32 pulls away from the membrane 22, the membrane 22 attached to the bottom plate 34 is deformed and an interior fluid chamber is formed pulling in fluid through valve 68. When the force from the heel strike is removed, the inherent properties of the material of the top plate 32 return the top plate 32 to its unflexed state. During the return of the top plate 32 to its unflexed state, the pump mechanism 65 expels fluid in the fluid chamber out of the valve 70. To meet the stiffness/flexibility, strength, and weight requirements needed for use on a prosthetic foot, the plates 32, 34 are made of a stiff but elastically bendable or deformable material such as carbon fiber, plastic, or metal.

As discussed, the pump mechanism 65 relies upon deformation of a membrane 22 to increase the volume of a fluid chamber located between the bottom surface of the housing 66 and the top surface of the membrane 22. The housing 66 surrounds the outer edge of the membrane 22 and creates an airtight seal with the membrane 22. The membrane and surrounding portion of the housing 66 rest within an opening in the top plate 32. The housing 66 has a lip which extends beyond the membrane 22 and surrounding portion of the housing to rest on the top surface of the top plate 32 and allows the top plate 32 to pull the housing 66 away from the membrane 22 when flexed.

The bottom surface of the housing 66 has two openings which extend into the housing to form internal passageways 84 to provide fluid communication between the internal fluid chamber and the two one-way valves 68, 70. The bottom surface of the housing 66 complements the top surface of the membrane 22 such that when no force is exerted on the pump mechanism 65 to expand the fluid chamber, the volume of the fluid chamber is zero or near-zero. As shown in FIG. 7B, both the bottom surface of the housing 66 and the top surface of the membrane 22 are preferably flat. The housing 66 may be formed of metal such as stainless steel or plastic or any other material which would provide sufficient strength to resist deformation or damage when pulled away from the membrane 22.

The pump mechanism 65 may be easily removed and reattached with no tools through a connector 86 on the membrane 22. The connector 86 is formed of an insert 88 having a circular end embedded in the membrane 22 and a fastener, such as a screw 90. The connector 86 anchors the membrane 22 to the bottom plate 34. The screw 90 having a circular end is used with the insert 88 to form the connector 86. The bottom plate 32 has two partially overlapping circular openings. The first circular opening is larger than the circular end of the screw 90 while the second circular opening is smaller than the circular end of the screw 90. To fixedly attach the pump mechanism 65 to the plates 32, 34 the screw 90 is inserted through the opening of the top plate 32 and then the first opening of the bottom plate 34 such that the lip of the housing 66 rests on the top plate 32. The user then slides the pump mechanism 65 into the smaller second circular opening and snaps the pump mechanism 65 into place. The insert 88 and the screw 90 may be formed of metal. Through the structure of the pump mechanism 65 and the plates 32, 34, the pump mechanism 65 has the benefit of being easily and quickly replaced.

The top plate 32 is provided with an opening 82 to enable easier flexion of the top blade near the attachment point 80. The size and shape of the opening 82 may be adjusted to change the force needed on the heel strike to flex the top plate 32. The attachment at attachment point 80 may be in a screw.

The heel element 76 is located between and attached to the two arms 42 of the top plate 32 which extend down either side of the foot 4, and the heel element 76 rests on the heel portion of the foot 4. The heel element 76 is preferably contoured such that the entirety of at least the outer edges of the bottom surface of the heel element 76 are in contact with the surface of the heel portion of the foot 4 upon which the heel element 76 rests. Through the contoured shape of the heel element 76 and the length and material of the top plate 32 and its two arms 42, the heel element 76 is held in place on the heel of the foot with no mechanical attachment between the heel element 76 and the heel of the foot.

To provide a lightweight pump mechanism 65 and pump mechanism on the prosthetic foot 4, the heel element 76 has an upper recess surrounded by raised edges 92. The raised edges 92 are formed such that the edges 92 provide a supporting surface for the curved ankle area of the foot 4. The edges 92 also control the maximum flexion of the top plate 32 and therefore, expansion of the pump mechanism 65.

As seen in FIGS. 7B and 7C, the raised edges 92 are contoured to receive the ankle area of the foot upon a heel strike. The heel element 76 is further provided with a plurality of slots 78 which extend through the heel element 76 to reduce the weight of the heel element 76. The slots 78 also allow particles or dirt to pass through the heel element 76 so the particles do not become trapped between the heel element 76 and the foot 4 and cause damage to the foot 4. The heel element 76 has a lower recess 94 on the bottom surface near the center which corresponds to space between the two blades of the prosthetic foot which form the heel.

An insert, which may have an "H" shape (not shown), fits between the blades of the heel and extends between the lower recess 94 of the heel element 76 and the blades of the heel. The insert may be formed of rubber and is used to provide a uniform pressure distribution from the heel of the foot 4 to the heel element 76. If the force on heel strike is only placed on one blade of the heel, some force is distributed to the other side and blade of the heel.

The embodiments described may be used with a prosthetic socket as described in U.S. Pat. No. 6,589,289 incorporated by reference and belonging to the assignee of this disclosure.

The embodiments described may be used with a prosthetic foot as described in U.S. Pat. No. 6,969,408 incorporated by reference and belonging to the assignee of this disclosure.

Figure 8:
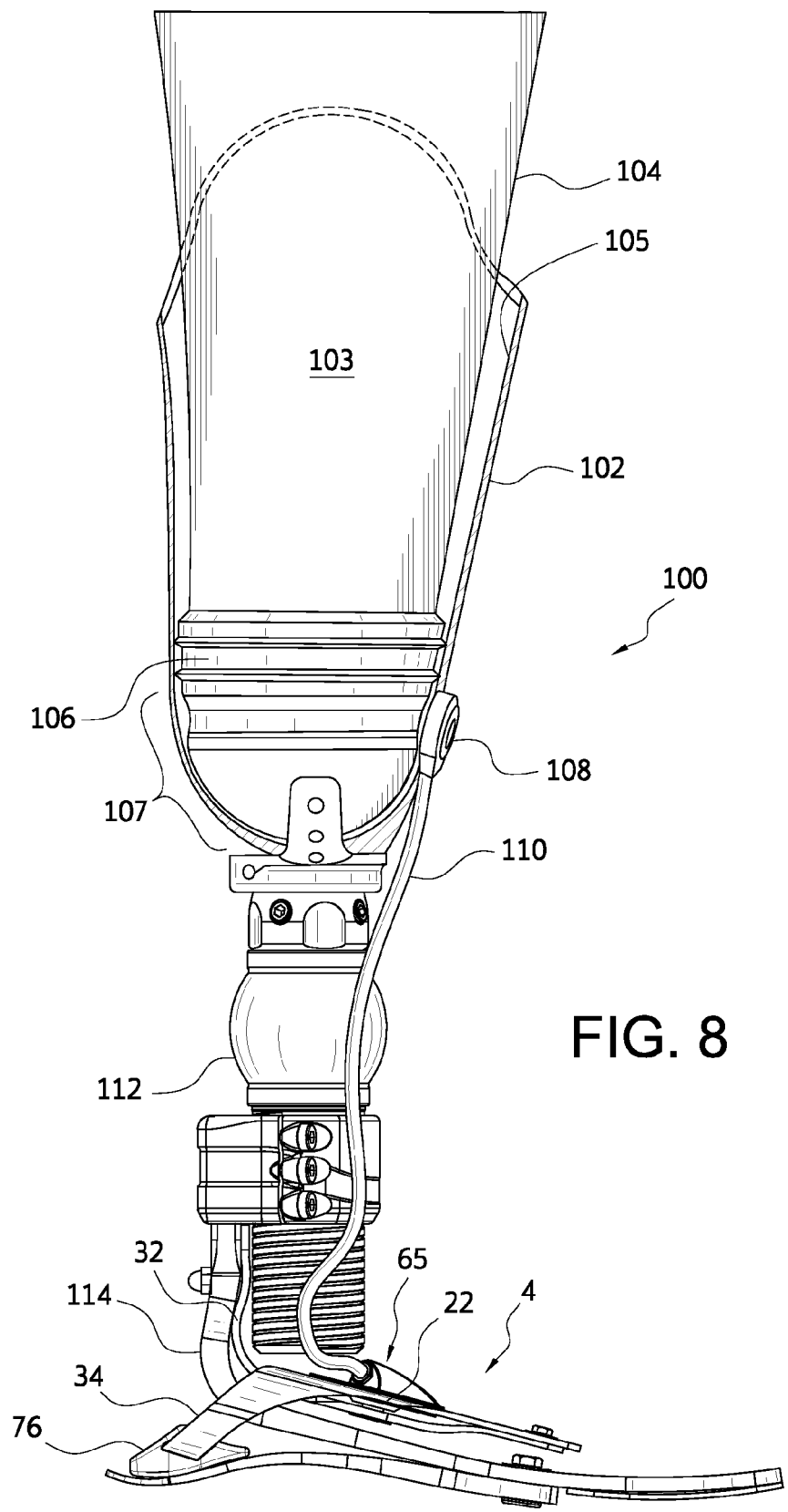
FIG. 8 is an elevational view showing a vacuum suspension system including the embodiment of FIG. 7A.

FIG. 8 illustrates a prosthetic device or a vacuum suspension system 100 including the pump mechanism 65 of FIG. 7A. The vacuum suspension system has a socket 102, a liner 104 preferably including a seal component 106, a valve 108, a tube 110 connecting the pump mechanism 65 to the socket 102, and a prosthetic foot 114. The socket defines an interior space 103, and interior walls 105 delimiting the interior space. The vacuum suspension system 100 may also employ a shock and/or rotation module 112. The shock and/or rotation module may be replaced with the connector and adapter system under the embodiment of FIG. 1.

The vacuum suspension system 100 provides improved proprioception and volume control. The vacuum suspension system 100 includes the pump mechanism 65, as discussed in earlier embodiments, which provides a vacuum assisted suspension by generating a negative pressure (vacuum) inside the socket 102. The function of the vacuum suspension system is fully automatic. The weight of the user is placed on the heel of the prosthetic foot 114 and expands the vacuum pump to efficiently draw air out of the socket in each step and expel it into the atmosphere during swing phase as the reservoir compresses again. The pump mechanism 65 creates a negative pressure inside the socket, resulting in a secure and reliable elevated vacuum suspension. The vacuum assisted suspension results in a secure and intimate suspension as the negative pressure formed inside the socket 102 within a vacuum zone 107 holds the liner 104 and the residuum firmly to the socket wall.

The vacuum suspension system 100 in combination with the liner 104 having a seal component 106 preferably at the proximal portion of the line allows for a transtibial amputee to move freely without pulling on the knee joint. This provides better comfort during daily activities and when sitting or driving.

The liner 104 may be of type including a seal component, preferably the liner with a seal component described in U.S patent application publication no. 2013/0053982, published on Feb. 28, 2013, incorporated by reference, and sold as the ICEROSS SEAL-IN V LINER by Össur hf. Other liners having a seal component may likewise be used including liners disclosed in U.S. Pat. No. 7,025,793, granted on Apr. 11, 2006, U.S. Pat. No. 7,909,884, granted on Mar. 22, 2011, U.S. Pat. No. 8,034,120, granted on Oct. 11, 2011, U.S. Pat. No. 8,052,760, granted on Nov. 8, 2011, and U.S. Pat. No. 8,097,043, granted on Jan. 17, 2012, and U.S. patent application Ser. No. 13/589,415, filed on Aug. 20, 2012. Each of these references is incorporated by reference. The vacuum suspension system is not limited to the liners mentioned above, and other liners whether with or without a seal may be employed.

The shock absorption from the rotation/shock module is independent of the pump module 4 which harvests a small amount of the heel motion for efficient vacuum generation. A rotation/shock module useable with the vacuum suspension system 100 is found in at least U.S. Pat. No. 6,478,826, granted on Nov. 12, 2002, U.S. Pat. No. 6,969,408, granted on Nov. 29, 2005, and U.S. Pat. No. 7,371,262, granted on May 13, 2008, incorporated by reference and belonging to the assignee of this disclosure. A commercial example of the foot and shock module may be the RE-FLEX SHOCK or RE-FLEX ROTATE sold by Össur hf of Reykjavik, Iceland.

Figure 11A:
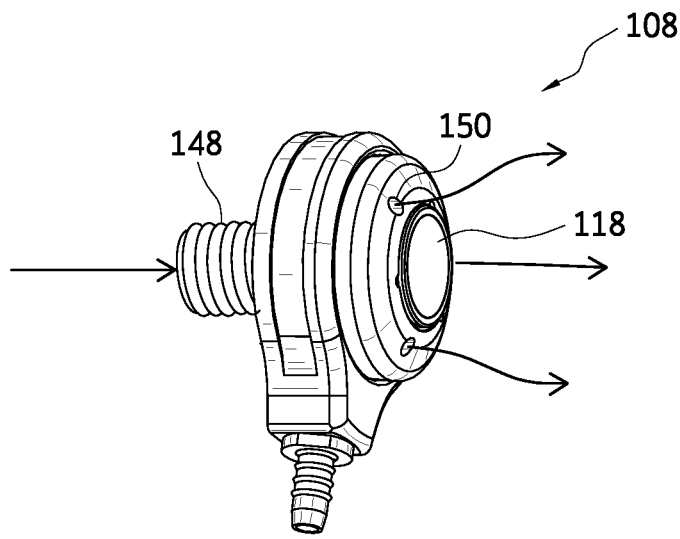
FIG. 11A is a schematic view of the tri-function valve of FIG. 9 in expulsion.
Figure 11B:
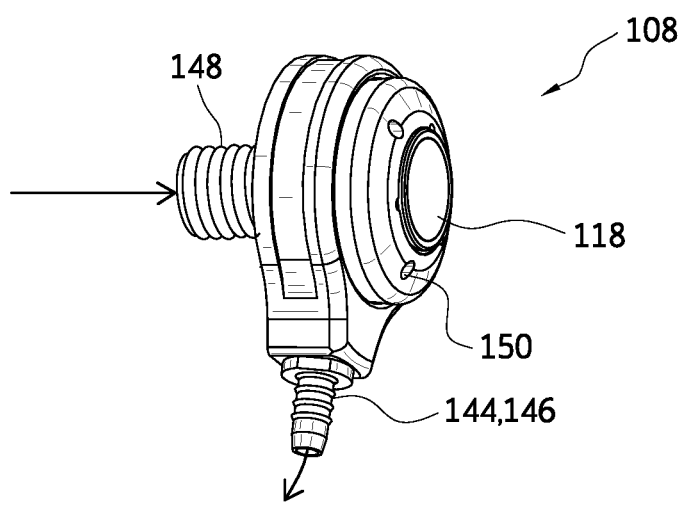
FIG. 11B is a schematic view of the tri-function valve of FIG. 10 in vacuum bypass.
Figure 11C:
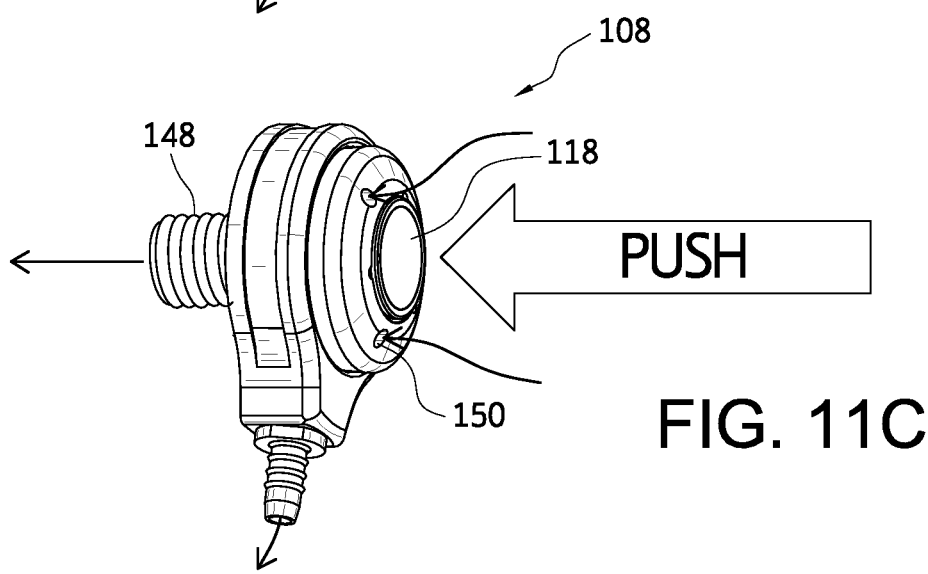
FIG. 11C is a schematic view of the tri-function valve of FIG. 9 in release.

FIGS. 9 and 10 illustrate an embodiment of the valve 108 for the vacuum suspension system 100. As shown in FIGS. 11A-11C, the valve 108 may be considered a tri-function valve in that it permits expulsion, vacuum bypass, and release.

FIG. 10 shows the valve 108 as having a cap or release button 118 and spring 120 inserted into a valve core 122, and interlocked by inserting a first o-ring or gasket 124 onto a smaller end of the release button 118 as it protrudes from the valve core 122. The cap key 116 is used to screw on or off the cap or release button 118 for checking the parts within the valve. A membrane 126 is inserted into an interior groove 152 formed on the valve core 122. A valve foam air filter 128 is inserted into a groove on a valve inner housing 130. The valve core 122 and the valve inner housing 130 are fastened to one another.

A second ring or gasket 132 and a third ring or gasket 134 are inserted into an interior groove 154 on a valve outer housing 136. A check valve 144 is inserted into an aperture 156 on the valve outer housing 136 and is interlocked with a tube connector 146.

The valve foam 138, screw 140 and valve insert 142 are used for mounting the valve 108 onto a socket. While the valve foam 138 and screw 140 may be removed after the socket is formed, the valve insert 142 remains on the socket and is used for coupling the valve 108 thereto. The shaft 148 of the valve inner housing 130 extends through an opening 158 of the valve insert 142 and into the socket 102 for fluid communication therewith for forming the vacuum.

The valve inner housing 130 is inserted into the valve outer housing 136. This arrangement of the valve outer housing 136 in combination with the gaskets used therewith is that the valve inner housing 130 and associated parts can be tightened or rotated regardless of the direction of the valve outer housing 136. The valve outer housing 136 can rotate relative to the socket with no loss of vacuum. This allows for accommodating any movement from the tube 110 coupled to the pump module 4 and the prosthetic foot 114.

As exemplified in FIGS. 11A-11C, FIG. 11A shows how the valve 108 permits expulsion of air through apertures 150 formed within the valve core 122, with air entering through the shaft 148, and exiting through the apertures 150. This arrangement allows the valve 108 to easily expel air from within the socket, for example, when the socket is donned.

FIG. 11B shows the valve 108 when it serves as a vacuum bypass. In this configuration, the air is expelled from the socket through the shaft 148 and is draw (by vacuum) through the tube connector 146 and check valve 144. The check valve 144 can maintain an airtight even if the tube connecting the pump module to the socket fails.

FIG. 11C shows an embodiment where pressing the release button 118 lets air into the socket and releases the vacuum, for example, so that the socket can be doffed. In this embodiment, the air enters through the apertures 150 and channels through the shaft 148 to introduce air into the socket.

Seventh Embodiment of the Prosthetic Device

FIG. 12 illustrates another embodiment of a pump mechanism 67 mounted on yet another different prosthetic foot 4. According to this embodiment, the prosthetic foot 4 includes a plate-like foot member 75 attached to a resilient heel member 77. A top mount 79 extends over the resilient heel member 77, and carries an adapter 9. An example of the prosthetic foot is described in greater in U.S. patent application Ser. No. 13/725,494, filed on Dec. 21, 2012, and commercially available as the FLEX-FOOT BALANCE by Össur hf. This patent is incorporated by reference and belongs to the assignee of this disclosure.

As shown in FIGS. 13A and 13B, the pump mechanism 67 is rocked back and forth as the foot plate 75 heel strikes (FIG. 13A) and toe strikes (13B). During a heel strike, as depicted in FIG. 13A, the membrane 22 is in a relaxed position and draws no vacuum from the socket via the tube 72. The one-way valve 70 only permits expulsion of air from the pump mechanism. During a toe strike, as depicted in FIG. 13B, the membrane 22 expands as it is pulled away from the top mount 79, and draws a vacuum (as evidenced by the arrow), whereas the air is expelled from the valve 70.

One will understand that the vacuum of this embodiment can be opposite of that of the embodiment depicted in FIGS. 7A-7C. In particular, FIGS. 13A-13B depict an embodiment where air is drawn out of the socket during a toe strike (FIG. 13B). In contrast, FIGS. 7A-7C depict an embodiment where air is drawn out of the socket during a heel strike.

In FIGS. 13A-13B, the membrane 22 is mounted under a plate section 166 of a rocker device 160. The rocker device 160 includes a bumper 162 at a first end and arranged for engaging the foot plate 75 at various phases of a walker's gait. A limiter 178 is provided under the plate section to limit rocking of the plate section 166. As the bumper 162 strikes the foot plate 75, an arm 164 extending from the bumper 162 and connecting to the plate section 166 causes the plate section 166 to draw away from the top mount 79. As the bumper 162 strikes the foot plate 75, an arm 164 extending from the bumper 162 and connecting to the plate section 166 causes the plate section 166 to draw away from the top mount 79.

Figure 14:
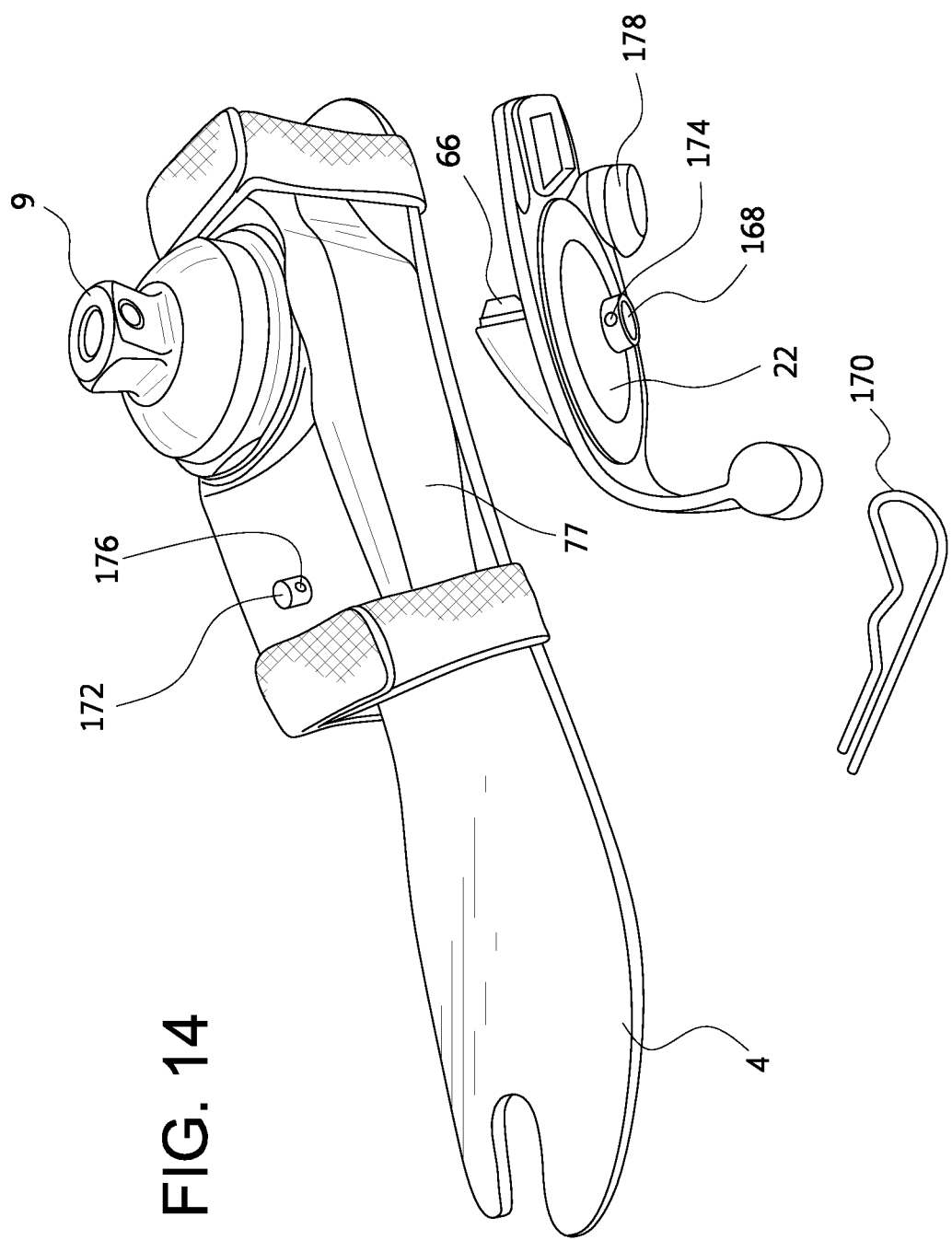
FIG. 14 is a disassembled view of the pump mechanism in FIG. 12.

FIG. 14 depicts the membrane 22 as having a coupling 168 with an aperture 174 and arranged to engage a pin 172 having an aperture 176, whereas the coupling 168 and pin 172 are retained by a spring lock 170. The coupling 168 is sized to permit pivoting of the pump mechanism 67 relative to the top mount 79.

The embodiments described may be used with a pressure regulator to insure the safety and comfort of the user which may be achieved using mechanical and/or electronic methods known in the industry.

While the foregoing embodiments have been described and shown, alternatives and modifications of these embodiments, such as those suggested by others, may be made to fall within the scope of the invention. The principles described may be extended to other types of prosthetic or orthopedic devices.

The invention claimed is:

1. A prosthetic system, comprising:
   a prosthetic foot;
   a pump mechanism including:
      a housing having first and second ports;
      a fluid chamber with a volume defined by an enclosure at least partially formed from a flexible material, an upper side of the fluid chamber in fluid communication with the first and second ports;
      a connector connected to a lower side of the enclosure;
   a first member connecting the pump mechanism to a proximal end of the prosthetic foot, the first member having an extending section extending freely over at least an ankle portion of a front surface of the prosthetic foot, the extending section movable relative to the prosthetic foot such that when weight of a user is applied to the prosthetic foot causing motion of the first member, a portion of the enclosure is shifted to increase the volume of the fluid chamber; and
   a second member connected to the first member and extending thereover, the pump mechanism mounted to the second member and the connector mounted to the first member, the fluid chamber changing in volume between the first and second members upon action of the prosthetic foot.

2. The system of claim 1, further comprising a tube connected to the first port.

3. The system of claim 2, wherein the first port is arranged to draw fluid through the tube due to the increase of volume of the fluid chamber.

4. The system of claim 1, wherein the second port includes a one-way valve.

5. The system of claim 1, wherein the increase in the volume of the fluid chamber occurs by deforming or extending a wall of the enclosure.

6. The system of claim 1, wherein the enclosure has two opposing walls connected by at least one side wall.

7. The system of claim 1, wherein the connector is formed of an insert attached to the enclosure.

8. A prosthetic system, comprising:
   a prosthetic foot;
   a pump mechanism including a housing having first and second ports, a fluid chamber with a volume defined by an enclosure at least partially formed from a flexible material, an upper side of the fluid chamber in fluid communication with the first and second ports, and a connector connected to a lower side of the enclosure and the prosthetic component;
   a prosthetic socket in fluid communication with the pump mechanism;
   a first member connecting the pump mechanism to of the prosthetic foot, the first member having an extending section movable relative to the prosthetic foot such that when weight of a user is applied to the prosthetic foot causing motion of the member, a portion of the enclosure is shifted to increase the volume of the fluid chamber and draw fluid from the prosthetic socket; and
   a second member connected to the first member and extending thereover, the pump mechanism mounted to the second member and the connector mounted to the first member, the fluid chamber changing in volume between the first and second members upon action of the prosthetic foot.

* * * * *